(12) United States Patent
Porter et al.

(10) Patent No.: US 8,598,344 B2
(45) Date of Patent: Dec. 3, 2013

(54) CDKI PATHWAY INHIBITORS AND USES THEREOF

(75) Inventors: Donald C. Porter, Columbia, SC (US); Igor B. Roninson, Lexington, SC (US); Mark P. Wentland, Watervilet, NY (US)

(73) Assignee: Senex Biotechnology, Columbia, SC (US)

( * ) Notice: Subject to any disclaimer, the term of this patent is extended or adjusted under 35 U.S.C. 154(b) by 0 days.

(21) Appl. No.: 12/956,420

(22) Filed: Nov. 30, 2010

(65) Prior Publication Data

US 2012/0071477 A1  Mar. 22, 2012

Related U.S. Application Data

(60) Provisional application No. 61/264,991, filed on Nov. 30, 2009, provisional application No. 61/323,400, filed on Apr. 13, 2010.

(51) Int. Cl.
   *C07D 239/72* (2006.01)
   *A01N 43/54* (2006.01)
   *A61K 31/517* (2006.01)

(52) U.S. Cl.
   USPC ........................ 544/293; 514/266.4

(58) Field of Classification Search
   USPC ........................ 514/266.4; 544/293
   See application file for complete search history.

(56) References Cited

U.S. PATENT DOCUMENTS 6,046,206 A * 4/2000 Pamukcu et al. ........ 514/266.21

FOREIGN PATENT DOCUMENTS

WO  WO 2011011522 A2 * 1/2011

OTHER PUBLICATIONS

Blair et al. Nature Chemical Biology, 2007 (3) p. 229-238 published on Mar. 4, 2007.*

* cited by examiner

*Primary Examiner* — Jeffrey S. Lundgren
*Assistant Examiner* — Michael Schmitt
(74) *Attorney, Agent, or Firm* — Wayne A. Keown; Furman Gregory Deptula

(57) ABSTRACT

The invention relates to compounds for inhibiting the Cyclin-Dependent Kinase Inhibitor (CDKI) pathway. More particularly, the invention relates to compounds for inhibiting the CDKI pathway for studies of and intervention in senescence-related and other CDKI-related diseases.

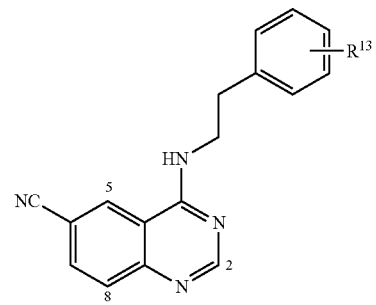

6 Claims, 10 Drawing Sheets

| Cmpd No | R⁶ | R⁴ | IC$_{50}$ (μM) |
|---|---|---|---|
| 1 | CN | (CH$_2$)$_2$Ph | 1.8 |
| 2 | Cl | (CH$_2$)$_2$Ph | 4.7 |
| 3 | I | (CH$_2$)$_2$Ph | 10.9 |
| 4 | CF$_3$ | (CH$_2$)$_2$Ph | 12.7 |
| 5 | F | (CH$_2$)$_2$Ph | 3.9 |
| 6 | NHAc | (CH$_2$)$_2$Ph | na |
| 7 | NO$_2$ | (CH$_2$)$_2$Ph | 2.9 |
| 8 | CN | (CH$_2$)$_2$CH$_3$ | 6.0 |
| 9 | CN | CH$_2$Ph | 3.3 |
| 10 | CN | CH$_2$CH(CH$_3$)$_2$ | 5.3 |
| 11 | CN | (CH$_2$)$_3$Ph | 4.7 |
| 12 | CN | CH$_2$-2,4-(OMe)$_2$C$_6$H$_4$ | 13.7 |
| 13 | CN | CH$_2$-3-NO$_2$C$_6$H$_5$ | 9.6 |
| 14 | CN | CH$_2$-2-napthyl | 1.8 |
| 15 | CN | CH$_2$-3,5-(CF$_3$)$_2$C$_6$H$_4$ | na |
| 16 | CN | CH$_2$-4-CF$_3$C$_6$H$_5$ | 6.5 |
| 17 | CN | CH$_2$-2,4-F$_2$C$_6$H$_4$ | 3.0 |
| 18 | CN | CH$_2$-3,4-F$_2$C$_6$H$_4$ | 3.0 |
| 19 | CN | CH(CH$_3$)Ph | 9.4 |

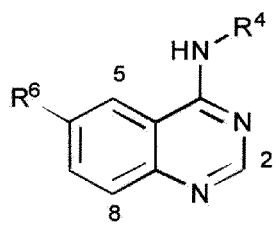

| Cmpd No | R⁶ | R⁴ | IC$_{50}$ (µM) |
|---|---|---|---|
| 20 | CN | CH$_2$-4-Cl-benzyl | 0.6 |
| 21 | CN | CH$_2$-4-F-benzyl | 1.07 |
| 22 | CN | CH$_2$-2-F-4-Br-benzyl | 1.96 |
| 23 | CN | CH$_2$-4-Nitro-benzyl | 2.57 |
| 24 | CN | CH$_2$-2-Cl-benzyl | 3.51 |
| 25 | CN | CH$_2$-4-Cl-2-F-benzyl | 1.17 |
| 26 | CN | (CH$_2$)$_2$-2-Naphthalen-2-yl | 1.03 |
| 27 | CN | CH$_2$-4-methoxy-benzyl | 2.65 |
| 28 | CN | CH$_2$-2,4-dichlorobenzyl | 1.20 |
| 29 | CN | CH$_2$-2-F,4-Cl-benzyl | 1.36 |
| 30 | CN | (CH$_2$)$_2$-2-naphthyl | 1.14 |
| 31 | CN | CH$_2$-4-methoxybenzyl | 2.34 |
| 32 | CN | CH$_2$-2,3,4-trifluorobenzyl | 1.90 |
| 33 | CN | CH$_2$-3-acetamidobenzyl | 0.90 |
| 34 | CN | CH$_2$-3-aminobenzyl | 2.21 |
| 35 | CN | (CH$_2$)$_2$-4-hydroxybenzyl | 2.17 |
| 36 | CN | (CH$_2$)$_2$-4-aminobenzyl | 0.73 |
| 37 | CN | (CH$_2$)$_2$-4-methylbenzyl | 2.09 |
| 38 | CN | (CH$_2$)$_2$-4-methoxybenzyl | 1.03 |
| 39 | CN | (CH$_2$)$_2$-4-F-benzyl | 1.38 |
| 40 | CN | CH$_2$-4-methylbenzyl | 1.69 |
| 41 | CN | (CH$_2$)$_2$-4-Cl-benzyl | 2.17 |
| 42 | CN | (CH$_2$)$_2$-4-dimethylaminobenzyl | 1.18 |
| 43 | CN | CH$_2$-3-naphthyl | 0.95 |
| 44 | methoxy | CH$_2$-benzyl | 11 |
| 45 | trifluoromethyl | CH$_2$-CH-(CH$_3$)$_2$ | 12.8 |
| 46 | morpholino | n-propyl | > 100 |
| 47 | NC(=O)benzyl | n-propyl | > 100 |

FIGURE 2

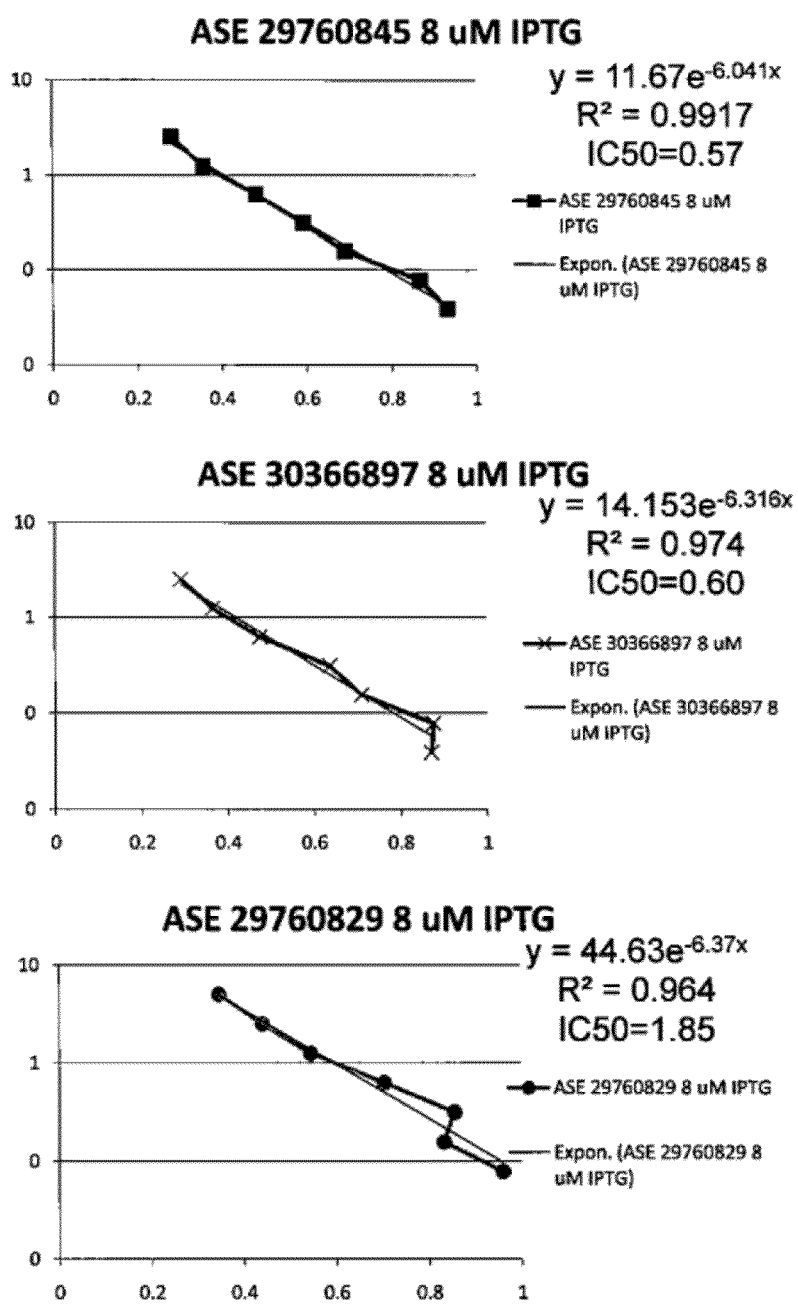
Figure 3 IC50 determination for lead compounds of SNX2 family.

Figure 4 Lead compound of SNX2 family inhibits the production of anti-apoptotic factors by irradiated/senescent fibroblasts.
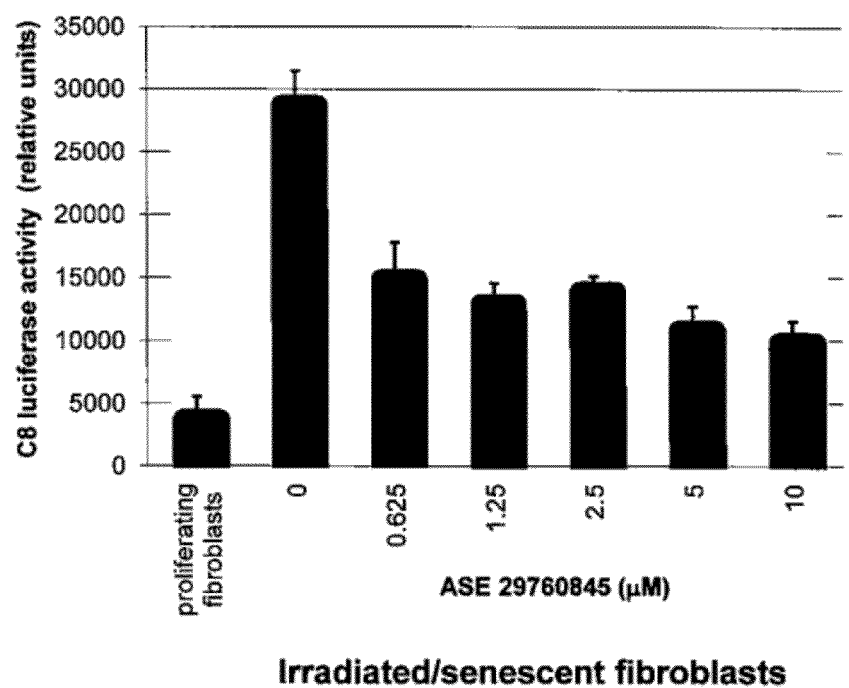

| SNX2-1-053 [μM] | Cell number [X 10⁶] | Viability [%] | FACS profile | p24+ [%] |
|---|---|---|---|---|
| 0 | 1.03 | 100 | | 42.8 |
| 0.3125 | 1.35 | 98.2 | | 35.8 |
| 0.625 | 0.95 | 90.5 | | 20.3 |
| 1.25 | 1.35 | 96.4 | | 16.5 |
| 2.5 | 0.45 | 72.0 | | 22.5 |
| 5 | 0.925 | 97.4 | | 15.7 |

*Figure 7*
SNX14
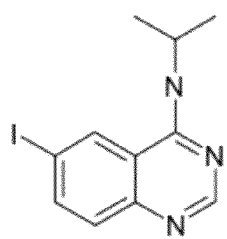
Compound 1
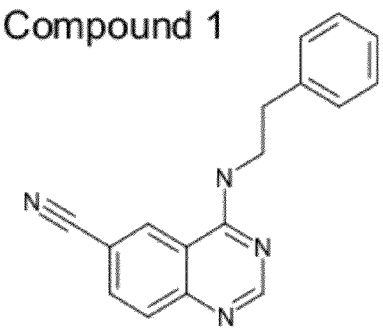
Compound 2
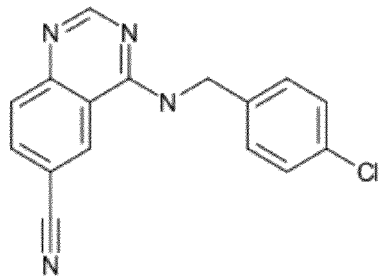
Compound 3
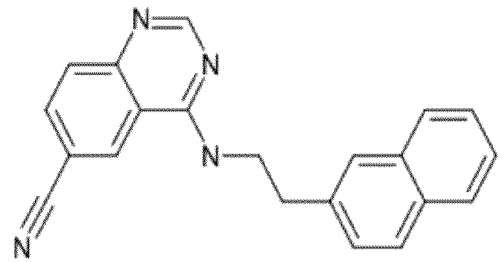
Compound 4 (87)
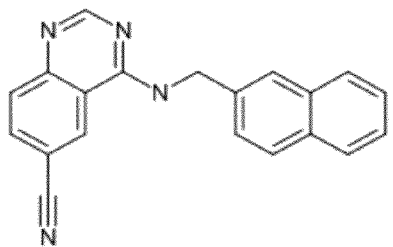
Compound 5 (104)
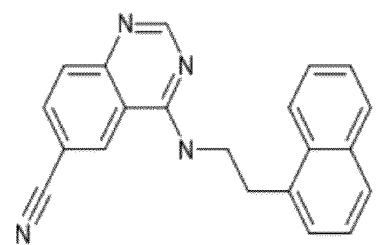

CDKI PATHWAY INHIBITORS AND USES THEREOF

BACKGROUND OF THE INVENTION

1. Field of the Invention

The invention relates to the inhibition of the Cyclin-Dependent Kinase Inhibitor (CDKI) pathway. More particularly, the invention relates to compounds and methods for inhibiting the CDKI pathway for studies of and intervention in senescence-related diseases, including degenerative diseases of the central nervous system, including Alzheimer's Disease and other dementias, as well as for studies of and intervention in cancer and viral diseases.

2. Summary of the Related Art

Cell senescence, originally defined as a series of cellular changes associated with aging, is now viewed more broadly as a signal transduction program leading to irreversible cell cycle arrest, accompanied by a distinct set of changes in the cellular phenotype (See e.g. Campisi, Cell 120: 513-522 (2005); Shay and Roninson, Oncogene 23: 2919-2933 (2004)). Senescence can be triggered by many different mechanisms including the shortening of telomeres (replicative senescence) or by other endogenous and exogenous acute and chronic stress signals, including major environmental factors, such as UV and cigarette smoke. The latter forms of telomere-independent senescence are variably referred to as accelerated senescence, STASIS (Stress or Aberrant Signaling Induced Senescence), or SIPS (Stress-Induced Premature Senescence). Regardless of the mode of induction, senescent cells develop the same general phenotype, characterized not only by permanent growth arrest but also by enlarged and flattened morphology, increased granularity, high lysosomal mass, and expression of senescence-associated endogenous β-galactosidase activity (SA-β-gal).

Dimri et al., Proc. Natl. Acad. Sci. USA 92: 9363-9367 (1995) teaches that in the human body, the phenotype of cell senescence has been detected in correlation with aging. Castro et al., Prostate 55: 30-38 (2003); Michaloglou et al., Nature 436: 720-724 (2005); and Collado et al., Nature 436: 642 (2005) teach that the phenotype of cell senescence has also been detected in pathological situations, including various pre-malignant conditions. te Poele et al., Cancer Res. 62: 1876-1883 (2002); and Roberson et al., Cancer Res. 65: 2795-2803 (2005) teach its detection in many tumors treated with chemotherapy.

In most systems of senescence that have been characterized at the molecular level, cell cycle arrest is triggered by the activation of p53, which in its turn induces a broad-specificity cyclin-dependent kinase inhibitor (CDKI) p21$^{Waf1/Cip1/Sdi1}$. p21 induction causes cell cycle arrest at the onset of senescence, but p53 and p21 levels decrease at a later stage. Shay and Roninson, Oncogene 23: 2919-2933 (2004) teach that this decrease is accompanied, however, by a stable increase in another CDKI protein, p16$^{Ink4A}$, which is believed to be primarily responsible for the maintenance of cell cycle arrest in senescent normal cells.

CDKI proteins act as negative regulators of the cell cycle and are therefore generally known as tumor suppressors. The induction of CDKI proteins, in particular p21, also occurs in tumor cells in the context of cancer therapy, in response to cellular damage by different classes of cancer chemotherapeutic drugs and ionizing radiation. Cell cycle arrest by CDKIs mediates the cytostatic and senescence-inducing activity of anticancer agents, one of the major components of their therapeutic effect (Roninson, *Cancer Res.*, 11, 2705-2715). Agents that would enhance the ability of CDKI proteins to induce cell cycle arrest will therefore be useful for the chemoprevention of cancer and for increasing the therapeutic efficacy of conventional anticancer agents.

Although senescent cells do not divide, they remain fully viable, metabolically and synthetically active. It has now been recognized that senescent cells secrete a variety of factors that have a major effect on their environment. Campisi, supra teaches that secretory activities of senescent cells have been linked to carcinogenesis, skin aging, and a variety of age-related diseases. A series of studies have implicated p21 and other CDKI proteins in disease-promoting activities of senescent cells. This insight came principally from the analysis by Chang et al., Proc. Natl. Acad. Sci. USA 97: 4291-4296 (2000) of the transcriptional effects of p21, expressed in a fibroblastoid cell line from an inducible promoter. This analysis showed that p21 produces significant changes in the expression of multiple genes. Many genes are strongly and rapidly inhibited by p21, and most of these are involved in cell proliferation. Zhu et al., Cell Cycle 1: 50-58 (2002) teaches that inhibition of cell cycle progression genes by p21 is mediated by negative cis-regulatory elements in the promoters of these genes, such as CDE/CHR. The same genes are downregulated in tumor cells that undergo senescence after chemotherapeutic treatment, but Chang et al., Proc. Natl. Acad. Sci. USA 99: 389-394 (2002) teaches that p21 knockout prevents the inhibition of these genes in drug-treated cells. Hence, p21 is responsible for the inhibition of multiple cell cycle progression genes in response to DNA damage.

Chang et al., 2000, supra teaches that another general effect of p21 induction is upregulation of genes, many of which encode transmembrane proteins, secreted proteins and extracellular matrix (ECM) components. This effect of p21 is relatively slow, occurring subsequently to growth arrest and concurrently with the development of the morphological features of senescence. These genes are induced by DNA damage but p21 knockout decreases their induction (Chang et al., 2002, supra). This decrease is only partial, which can be explained by recent findings by that the majority of p21-inducible genes are also induced in response to other CDKI, p16 and p27 (see WO 03/073062). Gregory et al., Cell Cycle 1: 343-350 (2002); and Poole et al., Cell Cycle 3: 931-940 (2004) teach that gene upregulation by CDKI has been reproduced using promoter constructs of many different CDKI-inducible genes, indicating that it occurs at the level of transcription. (Perkins et al., Science 275: 523-527 (1997); Gregory et al., supra; and Poole et al., supra teach that induction of transcription by p21 is mediated in part by transcription factor NFκB and transcription cofactors of p300/CBP family, but other intermediates in the signal transduction pathway that leads to the activation of transcription in response to CDKI—the CDKI pathway—remain presently unknown (FIG. 1).

Medical significance of the induction of transcription by CDKI has been indicated by the known functions of CDKI-inducible genes (Chang et al., 2000, supra). Many CDKI-upregulated genes are associated with cell senescence and organism aging, including a group of genes implicated in age-related diseases and lifespan restriction. One of these genes is p66$^{Shc}$, a mediator of oxidative stress, the knockout of which expands the lifespan of mice by about 30% (Migliaccio et al., supra). Many CDKI-induced genes play a role in age-related diseases, most notably Alzheimer's disease and amyloidosis. Thus, CDKI induce many human amyloid proteins, including Alzheimer's amyloid β precursor protein (βAPP) and serum amyloid A, implicated in amyloidosis, atherosclerosis and arthritis. CDKI also upregulate tissue transglutaminase that cross-links amyloid peptides leading to plaque formation in both Alzheimer's disease and amyloidosis. Some of CDKI-inducible genes are connective tissue growth factor and galectin-3 involved in atherosclerosis, as well as cathepsin B, fibronectin and plasminogen activator inhibitor 1, associated with arthritis. Murphy et al., J. Biol. Chem. 274: 5830-5834 (1999) teaches that several CDKI-inducible proteins are also implicated in an in vitro model of nephropathy. Remarkably, p21-null mice were found to be resistant to experimental induction of atherosclerosis (Merched and Chan, Circulation 110: 3830-3841 (2004)) and chronic renal disease (Al Douahji et al., Kidney Int. 56: 1691-1699 (1999); Megyesi et al., Proc. Natl. Acad. Sci. USA 96: 10830-10835 (1999).

In addition to their effect on cellular genes, CDKI stimulate the promoters of many human viruses, such as HIV-1, cytomegalovirus, adenovirus and SV40. Since many viruses induce p21 expression in infected cells, this effect suggests that promoter stimulation by CDKI may promote viral infections (Poole et al., supra).

Strong associations for CDKI-inducible genes have also been found in cancer. In particular, p21 expression activates the genes for many growth factors, inhibitors of apoptosis, angiogenic factors, and invasion-promoting proteases. In accordance with these changes in gene expression, Chang et al., 2000, supra teaches that p21-arrested cells show paracrine mitogenic and anti-apoptotic activities in coculture assays. Krtolica et al., Proc. Natl. Acad. Sci. USA 98: 12072-12077 (2001) teaches that paracrine tumor-promoting activities were demonstrated both in vitro and in vivo in CDKI-expressing normal senescent fibroblasts, which express p21 and p16. Importantly, senescent fibroblasts possess the characteristic pro-carcinogenic activity that has long been identified with tumor-associated stromal fibroblasts. Furthermore, all the experimental treatments shown to endow fibroblasts with tumor-promoting paracrine activities also induce CDKI, suggesting that the CDKI pathway could be the key mediator of pro-carcinogenic activity of stromal fibroblasts (Roninson, Cancer Lett. 179: 1-14 (2002)).

CDKI expression mediates cell cycle arrest not only in the program of senescence but also in numerous other situations, such as transient checkpoint arrest in response to different forms of damage, contact inhibition, and terminal differentiation. Hence, the CDKI pathway, which leads to the activation of multiple disease-promoting genes, is activated not only in cell senescence but also in many other physiological situations. As a result, CDKI-responsive gene products are expected to accumulate over the lifetime, contributing to the development of Alzheimer's disease, amyloidosis, atherosclerosis, arthritis, renal disease, viral diseases, including HIV/AIDS and cancer.

The effects of CDKIs are usually considered in light of their inhibition of cyclin-dependent kinases (CDKs), a family of serine/threonine kinases comprising 21 members in the human genome, which act in a complex with regulatory cyclin proteins. The best-known CDKs (CDK1, CDK2, CDK4, CDK6) are required for transitions between different phases of the cell cycle, but many other CDKs function as regulators of transcription or RNA processing rather than the cell cycle (Malumbres et al., 2009). Among the latter, of special relevance to the instant invention are CDK8 and a closely related CDK19 (80% overall identity, 98% identity in the ATP pocket). These CDKs, coupled with Cyclin C, are alternative components of a regulatory module of the Mediator complex that connects transcriptional regulators with RNA polymerase II to initiate transcription (Sato et al., 2004). CDK19 has been also called CDC2L6 and, confusingly, CDK11, but the name CDK11 is more often applied to two other proteins, presently known as CDK11A and CDK11B (Malumbres et al., 2009). CDK8 has been the subject of great attention in recent years and was identified as playing an important role in cancer (reviewed in Firestein and Hahn, 2009). CDK8 knockdown and knockout studies showed that it is not needed for cell growth but is required for early embryonic development (Westerling et al., 2007). CDK8 has been associated with processes involved in senescence and damage response: it regulates Smad transcriptional activation and turnover in BMP and TGF-β pathways (Alarcon et al., 2009) and acts as a stimulus-specific positive coregulator of p53 target genes (Donner et al., 2007). CDK8 has been identified as an oncogene amplified in ~50% of colon cancers, acting as a positive regulator of β-catenin, a transcription factor that plays a central role in colon carcinogenesis (Firestein et al., 2008; Morris et al., 2008). CDK8 has not yet been implicated in human diseases other than cancer.

In contrast to CDK8, little is known about CDK19, which substitutes for CDK8 in the corresponding Mediator modules but may have an opposite effect on the regulation of transcription. In particular, the study of Tsutsui et al. (2008), which refers to CDK19 as CDK11, reports that CDK19 acts as a negative regulator of viral activator VP16-dependent transcription, in contrast to CDK8 that acts as a positive regulator in this system. Pohlner and Von der Kammer (US patent publication 2009/00047274 A1) report that CDK19 (called there CDC2L6) is upregulated at the level of mRNA expression in the inferior temporal cortex and in the frontal cortex of the brains of patients with Alzheimer's disease (AD) relative to the brains of control individuals. It speculates that CDK19 (CDC2L6) could be used as a drug target for the treatment of AD but offers no evidence for that contention, aside from its overexpression in this disease.

US Patent Application Publication No. 20080033000 discloses a series of structurally related compounds, which inhibit the induction of all the tested genes by CDKI and also reverse CDKI-induced transcription. Those molecules showed little or no cytotoxicity in normal cells. As such, those molecules provided a promising starting point for developing useful new compounds and methods for inhibiting the CDKI pathway. Greater potency of such molecules is still needed.

A compound inhibiting CDK8 and CDK19 preferentially to other CDKs has been previously reported. This inhibitor is a steroidal alkaloid cortistatin A, isolated from the marine sponge *Corticium simplex*. The only biological properties reported for cortistatin A are its strong and highly selective antiproliferative activity against human umbilical vein endothelial cells (HUVECs) and its ability to inhibit vascular endothelial growth factor (VEGF)-induced migration and tubular formation of HUVECs (Aoki et al., 2007). In particular, cortistatin A inhibited the proliferation of HUVECs with $IC_{50}$ of 1.8 nm, whereas its antiproliferative activity against several other types of human cells was 6-7 μM, or >3,000-fold higher than for HUVECs. Cee et al. (2009) tested cortistatin A at 10 mm for the ability to inhibit a panel of 402 kinases (KinomeScan, Ambit Biosciences, San Diego, Calif.), and found that the strongest inhibition was observed for ROCK II (Percent of Control (POC)=0), CDK19 (termed there CDK11) (POC=0.1), and CDK8 (POC=0.95). The binding constants (Kd) were determined for CDK19 (Kd=10 nm), CDK8 (Kd=17 nm), and ROCK I and II (Kd=250 nm and 220 nm, respectively). It has been unknown whether the selective antiproliferative effect of cortistatin A against HUVECs is due to the inhibition of CDK19, CDK8 or ROCK (Cee et al., 2009). Based on its selective effect on endothelial cells, cortistatin A was proposed as a new type of anti-angiogenesis agent for the treatment of cancer (Aoki et al., 2007). However, the usefulness of anti-angiogenic agents for long-term therapy of chronic diseases other than cancer is doubtful, since clinical experience with angiogenesis inhibitors such as bevacizumab (Avastin), has revealed severe side effects (Grothey and Galanis, 2009), such as gastrointestinal perforation, inhibition of wound healing, and fatal pulmonary hemorrhage. Therefore, if any inhibitors of CDK8 could be found that don't have the strong anti-proliferative effect on endothelial cells, characteristic for cortistatin A, such inhibitors could be used for many clinical applications where angiogenesis inhibitors are precluded by their side effects.

There is, therefore, a need for more potent compounds and methods for inhibiting the CDKI pathway which may have a variety of clinical applications in chemoprevention and therapy of different age-related diseases. There is also a need for more potent compounds and methods for inhibiting CDKI pathway-mediated paracrine support for cancer development by senescent fibroblasts and for inhibiting viral replication. In addition there is a need for potent inhibitors of CDK8 that do not have strong anti-proliferative effects on endothelial cells.

BRIEF SUMMARY OF THE INVENTION

The invention provides compounds, pharmaceutical formulations and methods for treating degenerative diseases of the central nervous system (including Alzheimer's Disease and other dementias), cancer, viral diseases, atherosclerosis, arthritis and chronic renal disease.

In a first aspect, the invention provides new compounds having enhanced potency for inhibiting the induction of transcription by the Cyclin-Dependent Kinase Inhibitor (CDKI) pathway. Initially, the inventors used a high throughput screening system, described in greater detail in application number PCT/US06/01046, to screen over 100,000 drug-like small molecules from commercially available diversified compound collections. Through this screening, the present inventors identified a set of active compounds. (See US Patent Application Publication No. 20080033000.) These included a series of structurally related compounds, which inhibit the induction of all the tested genes by CDKI and also reverse CDKI-induced transcription. Those molecules showed little or no cytotoxicity in normal cells. Those molecules did not interfere with the cell cycle-inhibitory function of CDKIs and even enhanced the induction of G1 cell cycle arrest by CDKI proteins. Such compounds also blocked the development of the senescent morphology in fibroblasts arrested by DNA damage.

Based upon the above-described results, the present inventors have set out to develop new compounds that retain the benefits of those previously identified compounds while providing even greater potency.

In a second aspect, the invention provides methods for enhancing induction of G1 cell cycle arrest by CDKI proteins comprising contacting a cell with a compound that enhances the induction of G1 cell cycle arrest by CDKI proteins. In some preferred embodiments, the cell cycle-inhibitory activity of CDKI proteins is mediated by the inhibition of CDK8. The enhancement of the induction of G1 cell cycle arrest by CDKI proteins can be used for the chemoprevention and treatment of cancer and other diseases associated with abnormal cell proliferation and for increasing the ability of CDKI-inducing cancer therapeutic agents to arrest the growth of cancer cells. The method according to the invention comprises contacting a cell with a small molecule compound according to the invention.

In a third aspect the invention provides methods for inhibiting the production of tumor-promoting secreted factors by fibroblasts, comprising contacting the fibroblast with a compound according to the invention.

In a fourth aspect, the compounds and methods according to the invention are useful for treating a CDKI-mediated disease, including but not limited to Alzheimer's disease, atherosclerosis, amyloidosis, arthritis, chronic renal disease, viral diseases and cancer. Thus, the invention provides a method for treating or therapeutically treating a mammal having a CDKI-mediated disease comprising administering to the mammal a therapeutically effective amount of a compound according to the invention.

In a fifth aspect, the invention provides compounds that inhibit CDK8 to a greater extent than it inhibits certain other CDKs, and further inhibits CDK8 to a greater extent than it inhibits ROCK2.

In a sixth aspect, the invention provides methods for treating a mammal having a disease selected from degenerative diseases of the nervous system, including Alzheimer's Disease and other dementias, viral diseases, atherosclerosis, arthritis and chronic renal disease, the method comprising administering to the mammal a compound according to the fifth aspect of the invention.

In a seventh aspect, the invention provides methods for treating a mammal having a tumor that expresses β-catenin, the method comprising administering to the mammal a compound according to the fifth aspect of the invention.

BRIEF DESCRIPTION OF THE DRAWINGS

FIG. 2 shows the structures and $IC_{50}$ values for additional representative active compounds according to the invention.

FIG. 3 shows the effects of different doses of three active compounds on the stimulation of the CMV promoter activity by p21, represented as GFP expression from the CMV promoter in a reporter cell line carrying IPTG-inducible p21, normalized by cellular DNA content (a measure of cell number) as measured by Hoechst 33342 staining, in the presence or in the absence of two concentrations of IPTG.

FIG. 4 shows results of an assay for paracrine antiapoptotic activity of irradiated, senescent WI38 fibroblasts, as measured by the survival of C8 cells in low-serum media, in which irradiated, senescent WI38 fibroblasts were either untreated or treated with a compound according to the invention.

FIG. 7 shows structural formulae for compounds 1, 20, 26, 43 and SNX-14.

A. QPCR measurements (in triplicate) of CDK8 and CDK19 mRNA levels (arbitrary units) in cells that were either uninfected (no shRNA) or infected with recombinant lentiviruses, carrying either no insert (control) or shRNAs targeting CDK8 or CDK19, and used for infection at the indicated dilutions of packaging cell supernatant (1:8, 1:16 or 1:32).

B. FACS analysis of GFP expression in the same cells as in (A), with or without 3-day treatment with 50 μM IPTG, expressed as mean fluorescence intensity of the GFP-expressing live (propidium iodide negative) cells.

C. The same analysis as in (B), with GFP fluorescence normalized to cellular DNA amount (GFP/Hoechst) in microtiter wells assays (similar to FIG. 3).

D. The same analysis as in (C), except that cells were untreated or treated with 4 µM IPTG.

Figure 10:
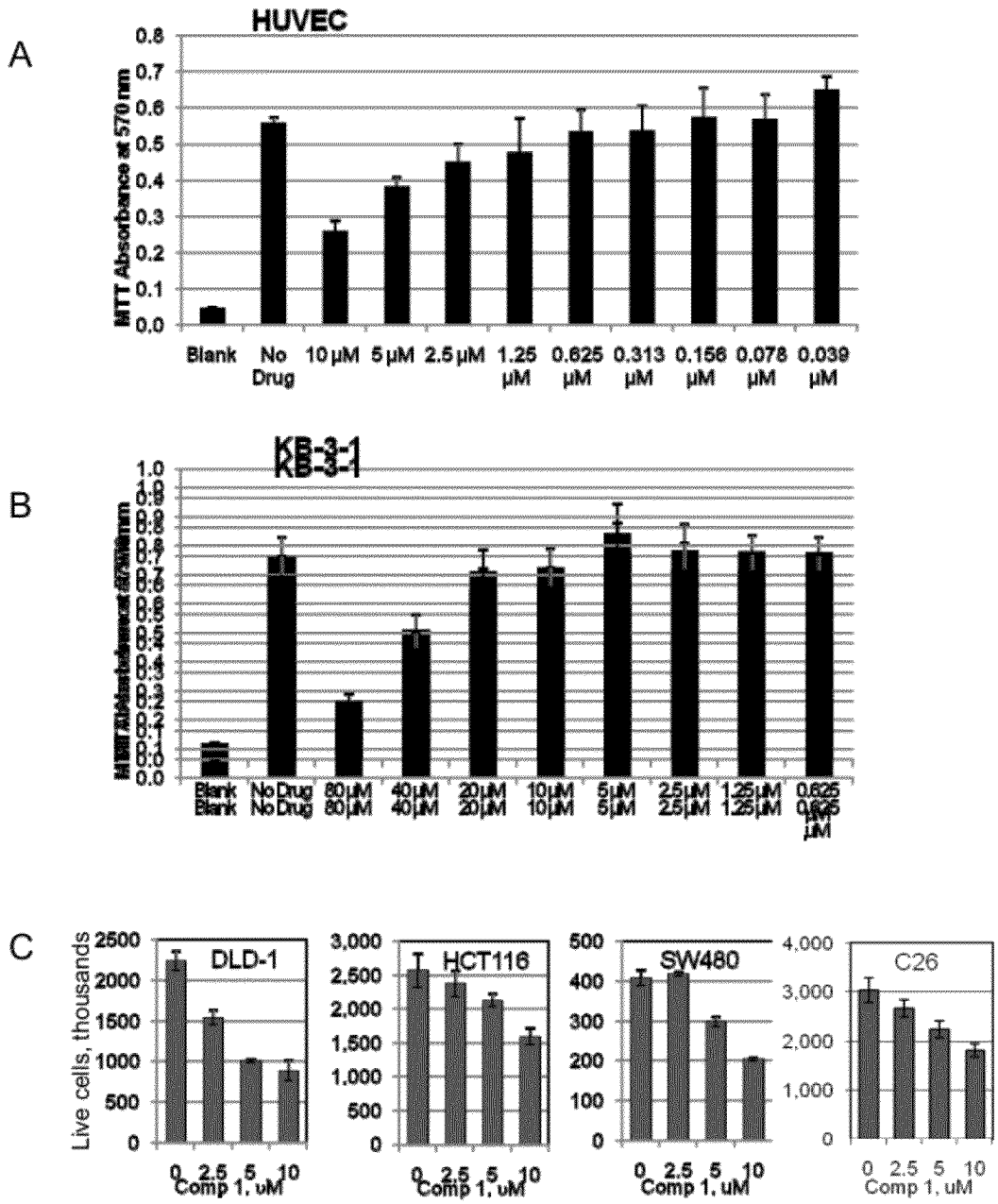

FIG. 10 shows effects of compound 1 on cell proliferation.

A. Effects of the indicated doses of compound 1 on the proliferation of HUVECs; relative cell number measured by MTT assay after 3 day exposure.

B. Effects of compound 1 on the proliferation of KB-3-1 carcinoma cells, measured as in (A).

C. Effects of compound 1 on proliferation of the indicated colon carcinoma cell lines, measured by FACS quantitation of the number of live (propidium iodide negative) cells.

DETAILED DESCRIPTION OF THE PREFERRED EMBODIMENTS

The invention relates to the inhibition of the Cyclin-Dependent Kinase Inhibitor (CDKI) pathway. More particularly, the invention relates to methods for inhibiting the CDKI pathway for studies of and intervention in senescence-related diseases and cancer. The patents and publications cited herein reflect the level of knowledge in this field and are hereby incorporated by reference in their entirety. Any conflict between the teachings of the cited references and this specification shall be resolved in favor of the latter.

The invention provides new compounds, pharmaceutical formulations and methods for treating degenerative diseases of the central nervous system, including Alzheimer's Disease and other dementias, as well as cancer, and viral diseases.

The invention provides compounds and methods for inhibiting the CDKI pathway which may have a variety of clinical applications in chemoprevention and therapy of different age-related diseases. The CDKI pathway inhibitors methods according to the invention show little or no cytotoxicity in normal cells. These molecules do not interfere with the cell cycle-inhibitory function of CDKIs and even enhance the induction of G1 cell cycle arrest by CDKI proteins. Compounds according to the invention block the development of the senescent morphology in fibroblasts arrested by DNA damage. They also inhibit the secretion of anti-apoptotic factors by CDKI-arrested cells. In some instances, the compounds of the invention are referred to herein as SNX2-class compounds.

In a first aspect, the invention provides novel compounds that inhibit the CDKI pathway. In certain embodiments, compounds according to the invention are represented by the formula (I-A):

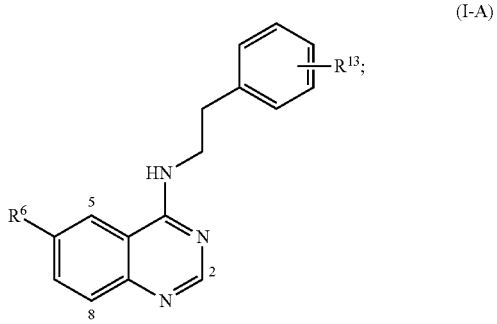

(I-A)

wherein $R^6$ is selected from CN, F, Cl, Br, I, $NO_2$, $CF_3$, CHO, $COR^{10}$, $CO_2R^{10}$, $CONR^{11}R^{12}$, $C(=S)NR^{11}R^{12}$, $C(=NR^{10})NR^{11}R^{12}$, $SOR^{10}$, $SO_2R^{10}$ and $SO_2NR^{11}R^{12}$, wherein $R^{13}$ is 2-, 3-, or 4-H, F, Cl, Br, I, OH, $OCH_3$, $CH_3$, $CF_3$, $NR^{11}R^{12}$, $CH_2R^{11}R^{12}$, $CO_2H$ and $CONR^{11}R^{12}$;

wherein $R^{10}$ is H or C1-C6 alkyl, and each $R^{11}$ and $R^{12}$ is independently H or C1-C6 alkyl, or $R^{11}$ and $R^{12}$ taken together form a ring;

provided however, that when $R^6$ is F then $R^{13}$ is not 4-OH or 4-Cl, when $R^6$ is Cl then $R^{13}$ is not 4-OH, 2-F, or 4-Cl, when $R^6$ is Br then $R^{13}$ is not H, 4-OH, 4-$SO_2NH_2$, 4-$OCH_3$, 3-F, or 4-Cl, when $R^6$ is I then $R^{13}$ is not 3-F or 2-Cl, and when $R^6$ is $NO_2$ then $R^{13}$ is not 3-F, 4-Cl, 4-Br, 4-I, 2-$OCH_3$, 3-$OCH_3$, 4-$OCH_3$, 4-$CONH_2$, 4-$CON(CH_3)_2$, or 4-$CO_2H$.

In certain embodiments, compounds according to the invention are represented by the formula (I-B):

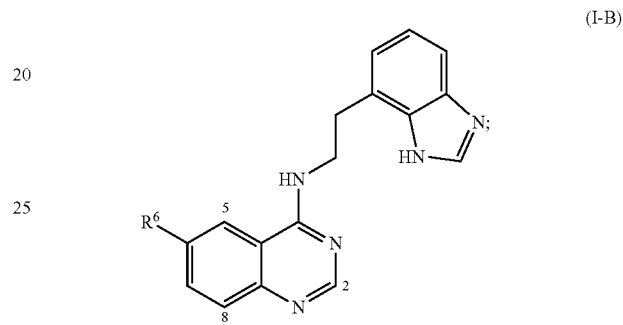

(I-B)

wherein $R^6$ is selected from CN, F, Cl, Br, I, $NO_2$, $CF_3$, CHO, $COR^{10}$, $CO_2R^{10}$, $CONR^{11}R^{12}$, $C(=S)NR^{11}R^{12}$, $C(=NR^{10})NR^{11}R^{12}$, $SOR^{10}$, $SO_2R^{10}$ and $SO_2NR^{11}R^{12}$, wherein $R^{13}$ is 2-, 3-, or 4-H, F, Cl, Br, I, OH, $OCH_3$, $CH_3$, $CF_3$, $NR^{11}R^{12}$, $CH_2R^{11}R^{12}$, $CO_2H$ and $CONR^{11}R^{12}$;

wherein $R^{10}$ is H or C1-C6 alkyl, and each $R^{11}$ and $R^{12}$ is independently H or C1-C6 alkyl, or $R^{11}$ and $R^{12}$ taken together form a ring.

In certain embodiments, compounds according to the invention are represented by the formula (I-C):

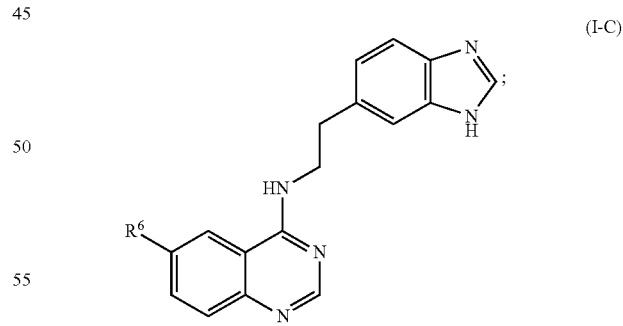

(I-C)

wherein $R^6$ is selected from CN, F, Cl, Br, I, $NO_2$, $CF_3$, CHO, $COR^{10}$, $CO_2R^{10}$, $CONR^{11}R^{12}$, $C(=S)NR^{11}R^{12}$, $C(=NR^{10})NR^{11}R^{12}$, $SOR^{10}$, $SO_2R^{10}$ and $SO_2NR^{11}R^{12}$, wherein $R^{13}$ is 2-, 3-, or 4-H, F, Cl, Br, I, OH, $OCH_3$, $CH_3$, $CF_3$, $NR^{11}R^{12}$, $CH_2R^{11}R^{12}$, $CO_2H$ and $CONR^{11}R^{12}$;

wherein $R^{10}$ is H or C1-C6 alkyl, and each $R^{11}$ and $R^{12}$ is independently H or C1-C6 alkyl, or $R^{11}$ and $R^{12}$ taken together form a ring.

In certain embodiments, compounds according to the invention are represented by the formula (II-A):

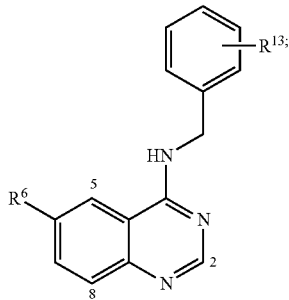

(II-A)

wherein $R^6$ is selected from CN, F, Cl, Br, I, $NO_2$, $CF_3$, CHO, $COR^{10}$, $CO_2R^{10}$, $CONR^{11}R^{12}$, $C(=S)NR^{11}R^{12}$, $C(=NR^{10})NR^{11}R^{12}$, $SOR^{10}$, $SO_2R^{10}$ and $SO_2NR^{11}R^{12}$;
wherein $R^{13}$ is 2-, 3-, or 4-H, F, Cl, Br, I, OH, $OCH_3$, $CH_3$, $CF_3$, $NR^{11}R^{12}$, $CH_2R^{11}R^{12}$, $CO_2H$ and $CONR^{11}R^{12}$;
wherein $R^{10}$ is H or C1-C6 alkyl, and each $R^{11}$ and $R^{12}$ is independently H or C1-C6 alkyl, or $R^{11}$ and $R^{12}$ taken together form a ring;
provided however, that when $R^6$ is CHO then $R^{13}$ is not H, when $R^6$ is Cl then $R^{13}$ is not 4-F or 4-$OCH_3$, when $R^6$ is Br then $R^{13}$ is not H, 2-Cl, 4-Cl, 4-$SO_2NH_2$, 4-$CO_2H$, 4-$OCH_3$, or 4-$CF_3$, when $R^6$ is I then $R^{13}$ is not H, 2-$CF_3$ or 3-$CF_3$, and when $R^6$ is $NO_2$ then $R^{13}$ is not H or 4-Cl.

In certain embodiments, compounds according to the invention are represented by the formula (II-B):

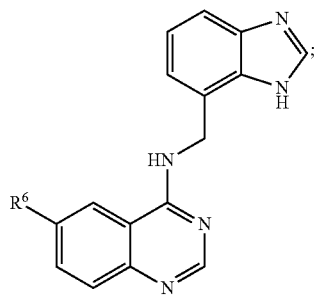

(II-B)

wherein $R^6$ is selected from CN, F, Cl, Br, I, $NO_2$, $CF_3$, CHO, $COR^{10}$, $CO_2R^{10}$, $CONR^{11}R^{12}$, $C(=S)NR^{11}R^{12}$, $C(=NR^{10})NR^{11}R^{12}$, $SOR^{10}$, $SO_2R^{10}$ and $SO_2NR^{11}R^{12}$;
wherein $R^{10}$ is H or C1-C6 alkyl, and each $R^{11}$ and $R^{12}$ is independently H or C1-C6 alkyl, or $R^{11}$ and $R^{12}$ taken together form a ring.

In certain embodiments, compounds according to the invention are represented by the formula (II-C):

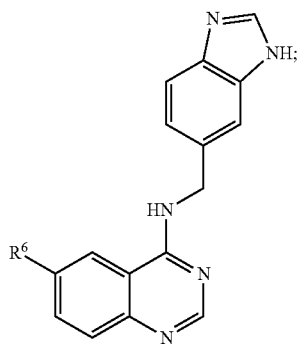

(II-C)

wherein $R^6$ is selected from F, Br, I, $NO_2$, $CF_3$, $COR^{10}$, $CO_2R^{10}$, $CONR^{11}R^{12}$, $C(=S)NR^{11}R^{12}$, $C(=NR^{10})NR^{11}R^{12}$, $SOR^{10}$, $SO_2R^{10}$ and $SO_2NR^{11}R^{12}$;

wherein $R^{10}$ is H or C1-C6 alkyl, and each $R^{11}$ and $R^{12}$ is independently H or C1-C6 alkyl, or $R^{11}$ and $R^{12}$ taken together form a ring.

In certain embodiments, compounds according to the invention are represented by the formula (III):

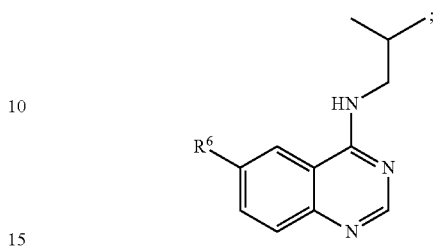

(III)

wherein $R^6$ is selected from CN, F, Cl, $NO_2$, $CF_3$, CHO, $COR^{10}$, $CO_2R^{10}$, $CONR^{11}R^{12}$, $C(=S)NR^{11}R^{12}$, $C(=NR^{10})NR^{11}R^{12}$, $SOR^{10}$, $SO_2R^{10}$ and $SO_2NR^{11}R^{12}$;
wherein $R^{10}$ is H or C1-C6 alkyl, and each $R^{11}$ and $R^{12}$ is independently H or C1-C6 alkyl, or $R^{11}$ and $R^{12}$ taken together form a ring.

In certain embodiments, compounds according to the invention are represented by the formula (IV-A):

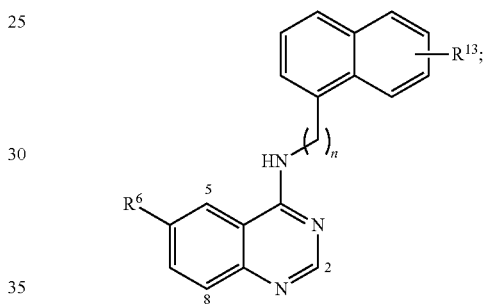

(IV-A)

wherein $R^6$ is selected from CN, F, Cl, Br, I, $NO_2$, $CF_3$, CHO, $COR^{10}$, $CO_2R^{10}$, $CONR^{11}R^{12}$, $C(=S)NR^{11}R^{12}$, $C(=NR^{10})NR^{11}R^{12}$, $SOR^{10}$, $SO_2R^{10}$ and $SO_2NR^{11}R^{12}$;
wherein $R^{13}$ is 2-, 3-, or 4-H, F, Cl, Br, I, OH, $OCH_3$, $CH_3$, $CF_3$, $NR^{11}R^{12}$, $CH_2R^{11}R^{12}$, $CO_2H$ and $CONR^{11}R^{12}$;
wherein $R^{10}$ is H or C1-C6 alkyl, and each $R^{11}$ and $R^{12}$ is independently H or C1-C6 alkyl, or $R^{11}$ and $R^{12}$ taken together form a ring; and
wherein n is from 1-3;
provided however that when $R^6$ is Br, I or $NO_2$ then $R^{13}$ is not H.

In certain embodiments, compounds according to the invention are represented by the formula (IV-B):

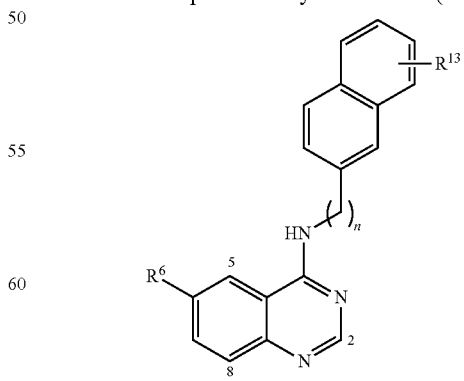

(IV-B)

wherein $R^6$ is selected from CN, F, Cl, Br, I, $NO_2$, $CF_3$, CHO, $COR^{10}$, $CO_2R^{10}$, $CONR^{11}R^{12}$, $C(=S)NR^{11}R^{12}$, $C(=NR^{10})NR^{11}R^{12}$, $SOR^{10}$, $SO_2R^{10}$ and $SO_2NR^{11}R^{12}$;

wherein $R^{13}$ is 2-, 3-, or 4-H, F, Cl, Br, I, OH, $OCH_3$, $CH_3$, $CF_3$, $NR^{11}R^{12}$, $CH_2R^{11}R^{12}$, $CO_2H$ and $CONR^{11}R^{12}$;
wherein $R^{10}$ is H or C1-C6 alkyl, and each $R^{11}$ and $R^{12}$ is independently H or C1-C6 alkyl, or $R^{11}$ and $R^{12}$ taken together form a ring; and
wherein n is from 1-3.

In certain embodiments, compounds according to the invention are represented by the formula (V):

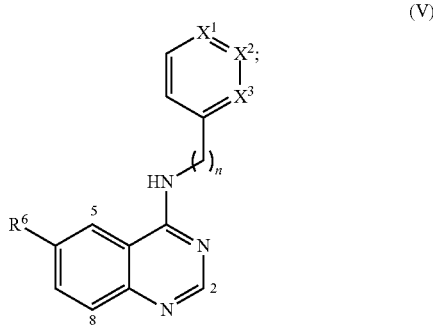

wherein each of $X^1$, $X^2$ and $X^3$ is independently N or CH, and one, but only one, of $X^1$, $X^2$ and $X^3$ is N;
wherein $R^6$ is selected from CN, F, Cl, Br, I, $NO_2$, $CF_3$, CHO, $COR^{10}$, $CO_2R^{10}$, $CONR^{11}R^{12}$, $C(=S)NR^{11}R^{12}$, $C(=NR^{10})NR^{11}R^{12}$, $SOR^{10}$, $SO_2R^{10}$ and $SO_2NR^{11}R^{12}$;
wherein $R^{13}$ is 2-, 3-, or 4-H, F, Cl, Br, I, OH, $OCH_3$, $CH_3$, $CF_3$, $NR^{11}R^{12}$, $CH_2R^{11}R^{12}$, $CO_2H$ and $CONR^{11}R^{12}$;
wherein $R^{10}$ is H or C1-C6 alkyl, and each $R^{11}$ and $R^{12}$ is independently H or C1-C6 alkyl, or $R^{11}$ and $R^{12}$ taken together form a ring; and
wherein n is from 1-3;
provided however, that when $X^1$ is N and n=1, then $R^6$ is not Br, when $X^2$ is N and n=1 then $R^6$ is not Br, I or CHO and when $X^3$ is N and n=1 then $R^6$ is not Br or CHO.

Figure 1:
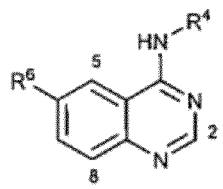
FIG. 1 shows the structures and $IC_{50}$ values for representative active compounds according to the invention.

In certain preferred embodiments the compounds according to the invention have the structures shown in FIG. 1 or FIG. 2.

In a second aspect, the invention provides methods for enhancing induction of G1 cell cycle arrest by CDKI proteins comprising contacting a cell with a compound having the structure (I-A), (I-B), (I-C), (II-A), (II-B), (II-C), (III), (IV-A), (IV-B), (V) or (VI):

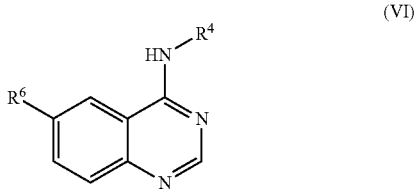

wherein $R^4$ is selected from C1-C6 alkyl and $C_{1-3}$—$R^{14}$, wherein $R^{14}$ is a 6 membered aryl or heteroaryl group or a fused bicyclic aryl or heteroaryl group, either of which may be optionally substituted with one or more substituent selected from 2-, 3-, or 4-H, F, Cl, Br, I, OH, $OCH_3$, $CH_3$, $CF_3$, $NR^{11}R^{12}$, $CH_2R^{11}R^{12}$, $CO_2H$ and $CONR^{11}R^{12}$, and wherein $R^6$ is an electron withdrawing group. In certain embodiments, the electron withdrawing group is selected from CN, F, Cl, Br, I, $NO_2$, $CF_3$, CHO, $COR^{10}$, $CO_2R^{10}$, $CONR^{11}R^{12}$, $C(=S)NR^{11}R^{12}$, $C(=NR^{10})NR^{11}R^{12}$, $SOR^{10}$, $SO_2R^{10}$ and $SO_2NR^{11}R^{12}$, wherein $R^{10}$ is H or C1-C6 alkyl, and each $R^{11}$ and $R^{12}$ is independently H or C1-C6 alkyl, or $R^{11}$ and $R^{12}$ taken together form a ring. In certain preferred embodiments, the small molecule has a structure selected from the group of structures shown in FIG. 1 or 2.

In a third aspect the invention provides methods for inhibiting the production of tumor-promoting secreted factors by fibroblasts, comprising contacting the fibroblast with a compound having the structure (I-A), (I-B), (I-C), (II-A), (II-B), (II-C), (III), (IV-A), (IV-B), (V) or (VI), including without limitation the compounds shown in FIG. 1 or 2. In certain embodiments, the fibroblast is in a mammal, including a human.

In a fourth aspect of the invention, the invention provides a method for treating or therapeutically treating a mammal having a CDKI-mediated disease comprising administering to the mammal an effective or therapeutically effective amount of a compound having the structure (I-A), (I-B), (I-C), (II-A), (II-B), (II-C), (III), (IV-A), (IV-B), (V) or (VI), including without limitation the compounds shown in FIG. 1 or 2. Preferred CDKI-mediated diseases include, without limitation, Alzheimer's disease, other dementias, amyloidosis, atherosclerosis, renal disease, viral diseases, and cancer. Preferred mammals include a human.

In certain embodiments the viral disease is human immunodeficiency virus (HIV) infection.

In a fifth aspect, the invention provides compounds that inhibit CDK8 to a greater extent than they inhibit certain other CDKs, and further inhibit CDK8 to a greater extent than they inhibit ROCK2. Such molecules are small molecules and do not include large molecules such as antisense oligonucleotides, siRNA, ribozymes, or proteins. In some embodiments, such compounds further inhibit CDK8 to a greater extent than ROCK1. In certain embodiments, the compound inhibits CDK8 to a greater extent than it inhibits CDK1. In certain embodiments, the compound inhibits CDK8 to a greater extent than it inhibits CDK1, CDK2, CDK4 and CDK6. In certain embodiments, the compound further inhibits CDK8 to a greater extent than CDK5, CDK7 and CDK9. In preferred embodiments, such greater extent is at least 2-fold, both for either set of CDKs and for ROCK2. In some embodiments, the compound further inhibits CDK8 to a greater extent than ROCK1, preferably by at least 2-fold. In some embodiments the comparison of inhibition of CDK8 with inhibition of ROCK2 or ROCK1 is carried out at a concentration of 10 μM compound. Extent of inhibition is measured by the assays taught in the Examples in this specification, including the assay conditions employed by the service providers utilized herein. Results of these assays are commonly expressed herein as percent of control (POC), with the control being no compound being present.

In a sixth aspect, the invention provides methods for treating or therapeutically treating a mammal having a disease selected from degenerative diseases of the nervous system, including Alzheimer's Disease and other dementias, viral diseases, atherosclerosis, arthritis and chronic renal disease, the method comprising administering to the mammal an effective amount or a therapeutically effective amount of a compound according to the fifth aspect of the invention.

In a seventh aspect, the invention provides methods for treating or therapeutically treating a mammal having a tumor that expresses β-catenin, the method comprising administering to the mammal an effective amount or a therapeutically effective amount of compound according to the fifth aspect of the invention.

Pharmaceutical Formulations and Administration

In the methods according to the invention, the compounds described above may be incorporated into a pharmaceutical formulation. Such formulations comprise the compound, which may be in the form of a free acid, salt or prodrug, in a pharmaceutically acceptable diluent, carrier, or excipient. Such formulations are well known in the art and are described, e.g., in Remington's Pharmaceutical Sciences, 18th Edition, ed. A. Gennaro, Mack Publishing Co., Easton, Pa., 1990.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art.

As used herein, the term pharmaceutically acceptable salts refers to salts that retain the desired biological activity of the above-identified compounds and exhibit minimal or no undesired toxicological effects. Examples of such salts include, but are not limited to, salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, palmoic acid, alginic acid, polyglutamic acid, naphthalenesulfonic acid, naphthalenedisulfonic acid, methanesulfonic acid, p-toluenesulfonic acid and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The active compound is included in the pharmaceutically acceptable carrier or diluent in an amount sufficient to deliver to a patient a therapeutically effective amount without causing serious toxic effects in the patient treated. A "therapeutically effective amount" is an amount sufficient to alleviate or eliminate signs or symptoms of the disease. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art. In certain applications, including without limitation, senile dementias such as Alzheimer's, an effective dose range for a 70 kg patient is from about 50 mg per patient per day up to about 10 grams per patient per day, or the maximum tolerated dose. In certain preferred embodiments the dose range is from about 200 mg per patient per day to about 10 g per patient per day. In certain preferred embodiments the dose range is from about 200 mg per patient per day to about 5 g per patient per day. The dose in each patient may be adjusted depending on the clinical response to the administration of a particular drug.

Administration of the pharmaceutical formulations in the methods according to the invention may be by any medically accepted route, including, without limitation, parenteral, oral, sublingual, transdermal, topical, intranasal, intratracheal, or intrarectal. In certain preferred embodiments, compositions of the invention are administered parenterally, e.g., intravenously in a hospital setting. In certain other preferred embodiments, administration may preferably be by the oral route.

The following examples are intended to further illustrate certain preferred embodiments of the invention and are not intended to limit the scope of the invention.

Example 1

Determination of $IC_{50}$ Values for CDKI-Pathway Inhibitor Compounds

The lead optimization series compounds have been tested for the ability to prevent the induction of transcription by p21 in HT1080 fibrosarcoma cells, as described in US20080033000. Briefly, the reporter cell line described in the above-referenced application, which carries IPTG (isopropyl-β-thio-galactoside)-inducible p21 gene together with a p21-inducible promoter driving the expression of Green Fluorescent Protein (GFP) was plated in 96-well plates, at 2000 cells per well for the no-IPTG arm of the assay and at 5000 cells per well for the IPTG arm of the assay. To induce the maximal levels of p21, IPTG was added to 50 μM concentration. Serial 2-fold dilutions of the tested compounds were added in quadruplicates to wells with and without IPTG, ~10 min after IPTG addition. After culturing under standard cell culture conditions for 72 hours, GFP fluorescence and Hoechst 33342 staining of cellular DNA (a measure of relative cell number) were measured as described in the previous application US20080033000, and IC50 values were calculated for each compound. The results of this analysis are presented in FIGS. 1 and 2.

To determine $IC_{50}$ values of the compounds at lower, more physiological levels of p21 induction, assays with selected compounds were repeated as described above, except that p21 was induced by a lower, 8 μM concentration of IPTG. The results of these assays for three active compounds of SNX2 family are shown in FIG. 3. The $IC_{50}$ values calculated in this assay are 570 nM for compound 1,600 nM for compound 14 and 1.85 μM for compound 3. These values are ~2-fold lower than the corresponding values determined for the same compounds in assays utilizing 50 μM IPTG, consistent with the different levels of p21 induced in two types of assays. The activities of compounds 1 and 14 exceed those of the most active of the previously disclosed compounds of US Patent Application Publication No. 20080033000 by an order of magnitude.

Example 2

Inhibition of Tumor-Promoting Activity of Irradiated, Senescent Fibroblasts

As discussed by Roninson (*Cancer Lett.* 179, 1-14, 2002), all the treatments known to induce the production of tumor-promoting secreted factors by cancer-associated stromal fibroblasts activate the CDKI pathway, including exposure to ionizing radiation and the induction of senescence. Since this pathway is the target of compounds according to the invention, such compounds may be the first agents to target tumor-supporting activities of cancer-associated fibroblasts. Some of the fibroblast-activating treatments include exposure to ionizing radiation and the induction of senescence through various means (Krtolica et al., *Proc. Natl. Acad. Sci. USA* 98, 12072, 2001). We have adopted a 96-well assay for anti-apoptotic activity that we have previously used with p21- expressing fibrosarcoma cells (Chang et al., *Proc. Natl. Acad. Sci. USA* 97, 4291-4296, 2000), to measure a tumor-promoting activity of normal proliferating fibroblasts and fibroblasts exposed to ionizing radiation and consequently developing the senescent phenotype. In this assay, WI38 fibroblasts are irradiated with 10 Gy using an MDS Nordion Gammacell 40 irradiator, or left unirradiated. The irradiated WI38 cells in suspension are added in triplicate to a 6-well tissue culture plate, at 250,000 cells per well, with and without the test compounds (used either at a single dose or at a series of concentrations from 0.3-10 µM). Unirradiated WI38 cells are plated at 125,000 cells per well, allowing them to reach the same density after growth over the time of the assay. On the third day, an apoptosis-sensitive murine transformed cell line C8, expressing firefly luciferase, is added to each well at 55,000 cells/well, and the cell mixtures are cultured overnight under standard conditions. On the next day (day 4), the media are replaced with media containing low (0.5%) FC2 serum and cultured for 3 days. On day 7, cells are lysed and the amount of luciferase activity associated with C8 cells is determined.

The results of such an assay carried out with compound 1 are shown in FIG. 4. In this experiment, co-culture with irradiated/senescent WI38 fibroblasts protects apoptosis-prone C8 cells from death under low serum culture conditions; the effect of irradiated WI38 fibroblasts is 6-fold higher than the corresponding effect of non-senescent WI38 cells. However, the addition of compound 1 greatly diminished this paracrine tumor-promoting effect of the irradiated/senescent fibroblasts (up to almost 3-fold). Hence, compounds according to the invention can inhibit production of tumor-supporting secreted factors by fibroblasts, indicating their utility in the treatment of different types of solid tumors.

Example 3

Inhibition of HIV Replication

The following assay was carried out by James McSharry at Ordway Research Institute at the request of Igor Roninson. HIV replication was assayed in a cell-to-cell model of HIV-1 transmission using chronically infected $H9_{IIIB}$ as donor cells cocultivated with uninfected CEM-ss leukemia cell line as recipient cells. 1 ml of RPMI1640 medium (+10% Fetal Bovine Serum+Penicillin/Streptomycin+glutamine) containing $10^4$ $H9_{IIIB}$ cells was mixed with 1 ml of the same medium containing $10^6$ CEM-ss cells. The mixture was spun at 1500 rpm for 5 min, the supernatant was aspirated, and cell pellets were suspended in 10 ml of the same media containing the following final concentrations of compound 1: 5, 2.5, 1.25, 0.625, 0.3125 and 0 µM (diluted from a stock solution of 500 µM in 25% DMSO). The suspended cells were placed into a 25 cm² flask and incubated at 37° C., 5% $CO_2$. On day 3, the cells were counted with a light microscope and an hemocytometer after trypan blue staining, which was used to determine the fraction of viable (trypan blue negative) cells. On day 5, the fraction of HIV-infected cells was determined using the K57-FITC conjugated monoclonal antibody to the HIV p24 antigen. For this measurement, the cells in each flask were mixed, 1 ml of cell culture was removed from each flask and placed into round bottom centrifuge tubes. The cells were separated from the medium by centrifugation at 1500 RPM for 5 minutes, the supernatants were aspirated and discarded and the cell pellets suspended in a fixative. After 15 min at room temperature, the cell pellets were washed with 3 ml of PBS, the cells were pelleted at 1500 RPM for 5 min, the supernatants discarded and the pellets permeabilized and then treated with the anti-p24 antibody. After a 15 minute incubation at room temperature in the dark, the monoclonal antibody was washed off with 3 ml of PBS and the cells collected by centrifugation at 1500 RPM for 5 min. The final pellets were suspended in 0.5 ml of PBS and the percentage of HIV p24-positive cells was determined by FACS analysis.

Figure 5:
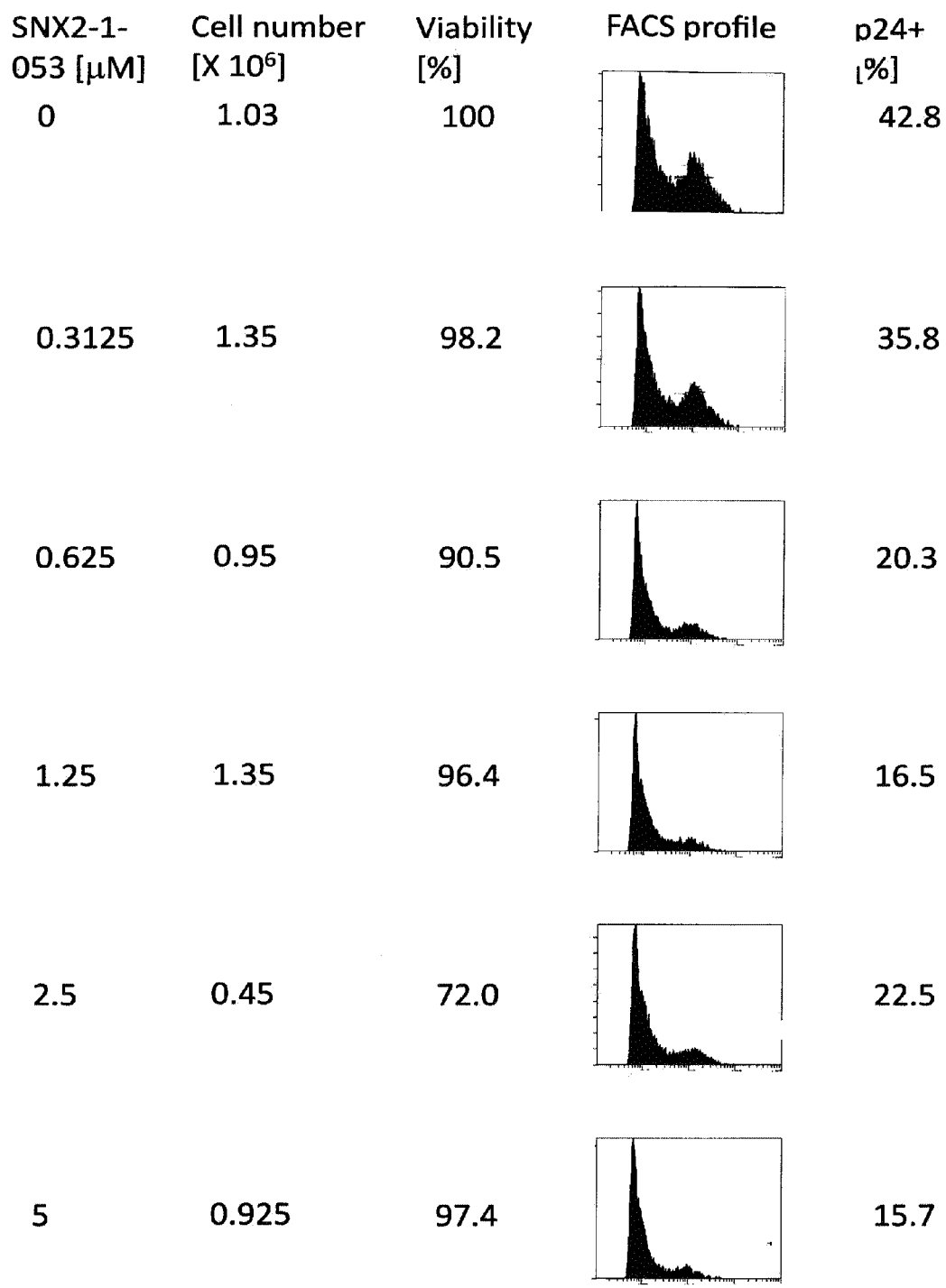
FIG. 5 shows inhibition of HIV-1 replication by a compound according to the invention.
Figure 6:
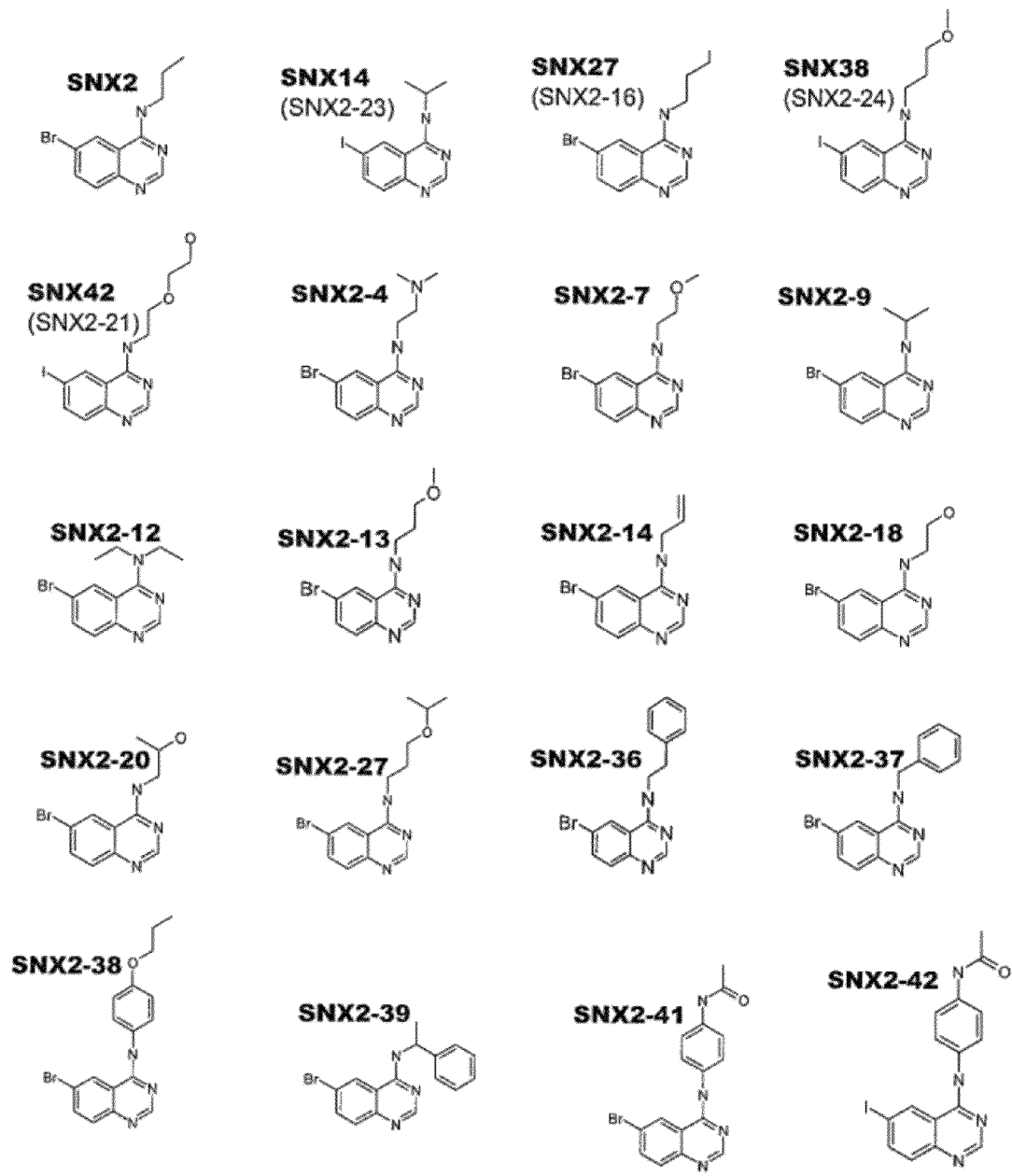
FIG. 6 shows structural formulae for compounds excluded from the claims.
Figure 8:
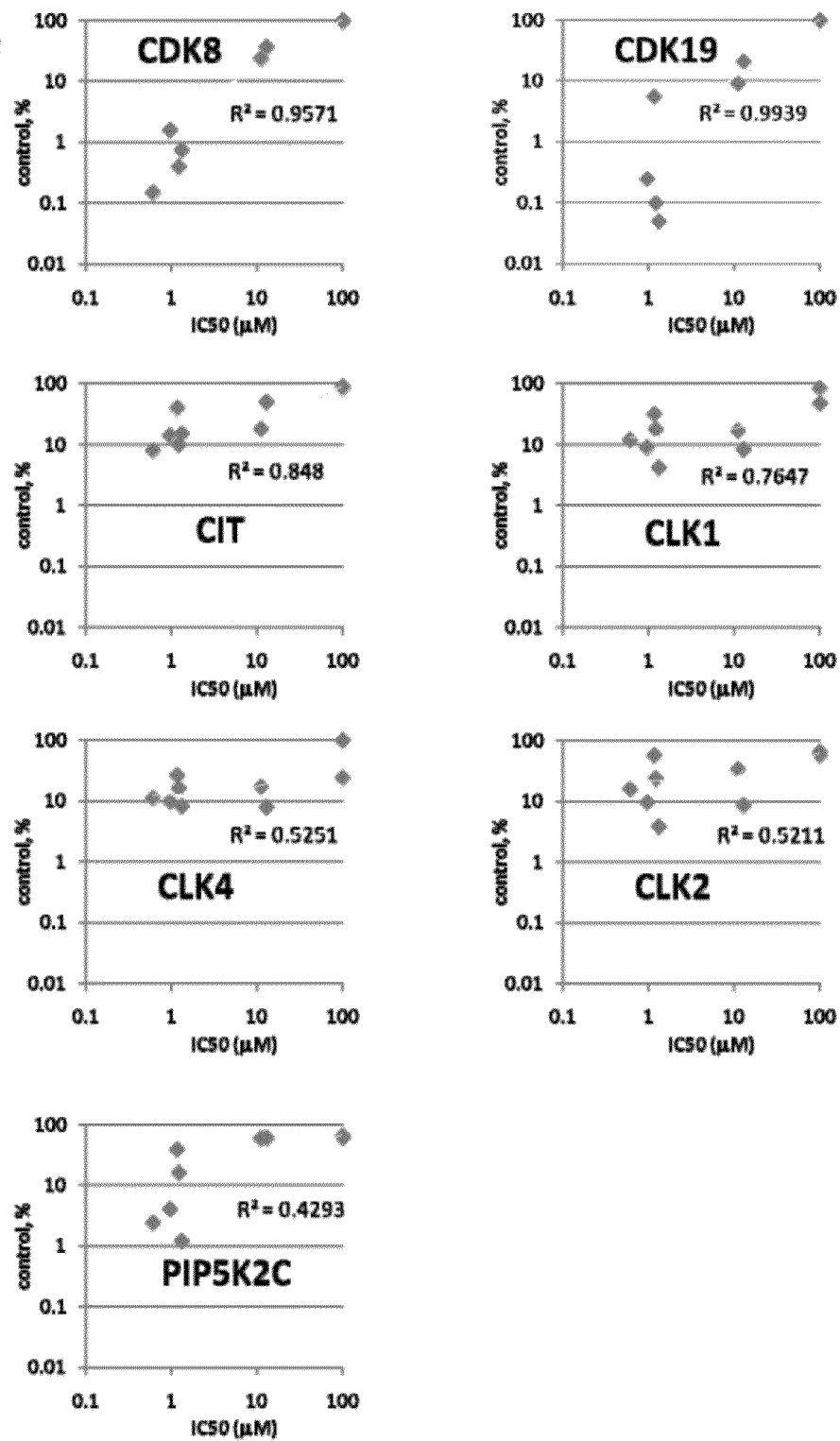
FIG. 8 shows correlations of IC50 values for nine SNX2-class compounds, as determined by the inhibition of CMV-GFP induction by p21, with the effect on the indicated kinases (% of control activity). The compounds were tested at 10 μM concentrations. The IC50 values for two compounds that showed no activity at the highest tested concentration (40 μM) are plotted as 100 μM.

The results of these assays are shown in FIG. 5. The addition of compound 1 produced a strong dose-dependent decrease in the fraction of HIV-infected (p24-positive) cells, with the calculated EC50 of 0.58 µM. Thus, the CKI pathway inhibitor is capable of inhibiting viral (HIV) replication.

Example 4

Selective Inhibition of CDK8 and CDK19 by SNX2-Class Compounds

FIG. 7 shows the structures of six specific SNX2-class compounds, including SNX14, the most potent pre-existing structure of SNX2 class disclosed in US Patent Application 2009/0281129, as well as compounds 1, 14, 20, 26, and 43 created by the instant inventors and disclosed in U.S. Patent Application 61/264,991. Table 1 shows the $IC_{50}$ values for the activities of these compounds in a cellular assay for CDKI pathway inhibition, which is described in our previous patent application. This assay is based on the induction of green fluorescent protein (GFP) expression from the cytomegalovirus (CMV) promoter in human HT1080 fibrosarcoma cells that express CDKI p21 from an isopropyl-(3-thio-galactoside (IPTG)-inducible promoter. The compound activity as a CDKI pathway inhibitor is measured by its ability to prevent the stimulation of the CMV promoter upon the addition of p21-inducing IPTG. CMV promoter activity is measured by the ratio of GFP fluorescence to the relative cell number, as determined by staining cellular DNA with Hoechst 33342. This assay was conducted in two modes. In the first mode p21 is induced to the maximal level, using 50 µM IPTG. In the second mode, lower, more physiological levels of p21, are induced by a lower IPTG concentration (2 µM). The $IC_{50}$ values are presented in Table 1, where the tested compounds show 2-3 times higher potency (lower $IC_{50}$) in the 2-µM IPTG than in the 50-µM IPTG assay.

TABLE 1

Activities of some SNX2-class compounds.

| | $IC_{50}$ or Kd (nM) | | | | | |
|---|---|---|---|---|---|---|
| Assay Compound | SNX14 | Compound 1 | Compound 20 | Compound 26 | Compound 43 | Compound 14 |
| Cell-based assay ($IC_{50}$) | 6430 | 641 | 199 | 769 | 220 | 2540 |
| CDK8 inhibition (Kd) | 10000 | 830 | 240 | 570 | 240 | 2500 |
| CDK19 inhibition (Kd) | 3800 | 310 | 99 | 160 | 190 | 1100 |

SNX2-class compounds are 4-aminoquinazolines, and such structures are a part of the pharmacophore for several protein kinase inhibitors, such as EGF receptor inhibitor gefitinib (Notably, we have tested gefitinib in our assays and found it inactive for CDKI pathway inhibition). This similarity led us to test SNX14 for the ability to inhibit 285 kinases, using the services of KinaseProfiler of Millipore Corporation (285 kinases). Subsequently, compound 1 was tested for the inhibition of a larger panel of 442 kinases, using the services of KinomeScan, a division of Ambit Biosciences, San Diego, Calif. The KINOMEscan assay has been described in detail in Fabian et al., Nat. Biotechnol. 23: 329 (2005) and Karaman et al., Nat. Biotechnol. 26: 127 (2008).

The KinomeScan assay is based on a competition binding assay that quantitatively measures the ability of a compound to compete with an immobilized, ATP site directed ligand. The assay is performed by combining three components: DNA-tagged kinase; immobilized ligand; and a test compound. The ability of the test compound to compete with the immobilized ligand is measured via quantitative PCR of the DNA tag. The compounds (tested at 10 μM) showed significant inhibition of a number of kinases, with the more potent compound 1 showing the strongest inhibition (>99%) for CDK19 (0.05 percent of control (POC) binding) and CDK8 (0.25 POC) in the KinomeScan assay. No other members of the CDK family were inhibited to a comparable degree. The CDKs tested by Millipore for inhibition with SNX14 included CDK1, CDK2, CDK3, CDK5, CDK7 and CDK9; none of these were inhibited to less than 49 percent of control (POC) activity. The CDKs tested by KinomeScan for the effect of Compound 1 included CDK2, CDK3, CDK4, CDK5, CDK7, CDK8, CDK9 and CDK19; aside from CDK8 and CDK19, the strongest inhibited CDK was CDK7 (33% POC binding). To determine the inhibition of which kinases correlates with the biological activity of SNX2-class compounds, we tested eight additional compounds of the SNX2 family, which gave different $IC_{50}$ values in the cellular assays, for the ability to affect 24 kinases that were most susceptible to compound 1, through the services of KinomeScan. Table 2 shows the results of this analysis, where the effect on the corresponding kinases is expressed as POC for the ligand binding by the corresponding enzymes in the presence of 10 μM of each of the tested compounds, together with $IC_{50}$ values for the corresponding compounds as determined in the cellular assay. (The $IC_{50}$ values shown for SNX14 and compounds 1 and 20 in Table 2 differ from the corresponding values in Table 1 not only because they were determined in separate assays, but also because the $IC_{50}$ values in Table 2 were calculated on the assumption that the maximal effect of a compound corresponds to zero GFP/Hoechst value, whereas the $IC_{50}$ values in Table 1 are calculated on the basis of the maximal inhibition produced by the highest doses of the tested compound.) FIG. 4 plots $IC_{50}$ values versus POC for seven of the most sensitive kinases in Table 2. CDK8 and CDK19, but not the other tested kinases, showed excellent correlation between $IC_{50}$ in the cellular assay and POC in the kinase assay ($R^2$=0.96 and 0.99, respectively). Both CDK8 and CDK19 were inhibited >98% by five of the most potent compounds tested in this assay, except for compound 26 (FIG. 2), which affected CDK8 by almost 100% but CDK19 by 94.6%; all the other compounds affected CDK19 more than CDK8. Compound 26 also shows higher selectivity than the other tested compounds for CDK8 and CDK19 relative to the other tested kinases. We have also determined the binding constant (Kd) for SNX14, compound 1, compound 20, compound 26, compound 43 and compound 14 in kinase assays for CDK8 and CDK19 (Table 1).

TABLE 2

Inhibition of different kinases by SNX2-class compounds.

| | Compound | | | | | | | | |
|---|---|---|---|---|---|---|---|---|---|
| | 1 | 20 | 26 | 43 | 14 | 44 | 45 | 46 | 47 |
| IC50 | 1.3 | 0.6 | 1.15 | 0.95 | 1.2 | 11 | 12.8 | >100 | >100 |
| Kinase | | | | | | | | | |
| CDK19 | 0.05 | 0 | 5.6 | 0.25 | 0.1 | 9.2 | 21 | 100 | 100 |
| CDK8 | 0.75 | 0.15 | 0 | 1.6 | 0.4 | 24 | 37 | 100 | 100 |
| PIP5K2C | 1.2 | 2.4 | 39 | 4 | 16 | 59 | 60 | 61 | 65 |
| CLK2 | 3.8 | 16 | 58 | 9.6 | 24 | 34 | 8.6 | 66 | 58 |
| CLK1 | 4.2 | 12 | 32 | 9 | 18 | 17 | 8.4 | 48 | 84 |
| STK16 | 4.2 | 25 | 16 | 30 | 2.4 | 70 | 17 | 80 | 100 |
| YSK4 | 5.4 | 31 | 44 | 29 | 21 | 39 | 41 | 91 | 79 |
| CLK4 | 8 | 11 | 26 | 9.6 | 16 | 17 | 7.8 | 24 | 100 |
| PIK3CG | 8 | 40 | 58 | 35 | 35 | 88 | 82 | 94 | 98 |
| IRAK1 | 8.2 | 26 | 89 | 7.6 | 35 | 64 | 25 | 81 | 100 |
| SLK | 11 | 61 | 73 | 92 | 90 | 43 | 59 | 88 | 100 |
| MAP4K2 | 12 | 21 | 28 | 28 | 16 | 35 | 12 | 82 | 66 |
| EGFR (G719C) | 13 | 34 | 68 | 53 | 92 | 0.85 | 59 | 61 | 55 |
| BTK | 15 | 100 | 100 | 100 | 100 | 100 | 100 | 81 | 100 |
| CIT | 15 | 7.9 | 40 | 14 | 9.8 | 18 | 50 | 86 | 90 |
| MAPKAPK5 | 15 | 92 | 100 | 85 | 100 | 94 | 100 | 91 | 95 |
| CSNK1G2 | 16 | 62 | 57 | 53 | 43 | 80 | 53 | 55 | 72 |
| CSNK1G3 | 16 | 82 | 50 | 54 | 52 | 84 | 50 | 100 | 56 |
| PIK3CA (I800L) | 17 | 73 | 81 | 87 | 62 | 86 | 83 | 83 | 58 |
| HIPK2 | 18 | 28 | 73 | 30 | 34 | 62 | 20 | 30 | 78 |
| HIPK3 | 18 | 28 | 66 | 42 | 35 | 53 | 28 | 34 | 75 |
| MEK3 | 18 | 76 | 78 | 64 | 29 | 72 | 71 | 100 | 100 |
| MEK5 | 18 | 62 | 61 | 41 | 13 | 59 | 46 | 17 | 36 |
| FLT3 (D835Y) | 19 | 69 | 55 | 76 | 32 | 55 | 4.7 | 19 | 93 |

Example 5

Mediation of the CDKI Pathway by CDK8, but not by CDK19

Figure 9:
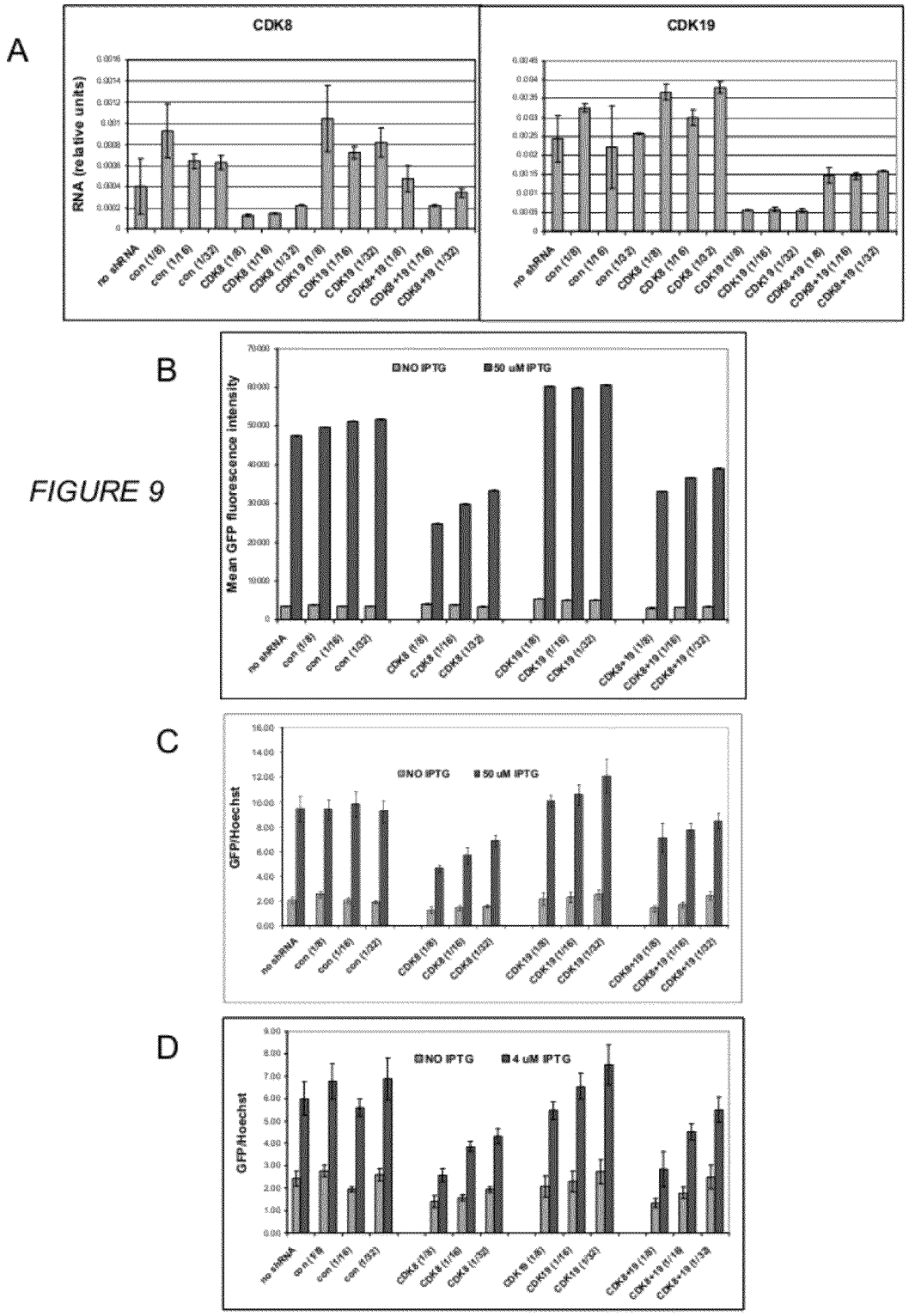
FIG. 9 shows results of shRNA analysis of the role of CDK8 and CDK19 in the CKI pathway in HT1080 cells with IPTG-inducible p21 and p21-responsive CMV-GFP promoter.

To test the role of CDK19 and CDK8 in the CDKI pathway, we have decreased the expression of these genes through RNA interference (RNAi) using lentiviral vectors expressing short hairpin RNA (shRNA) targeting the corresponding genes and cloned in the pLKO.1 vector backbone (Open Biosystems, Huntsville, Ala.). The CDK8 mRNA sequence targeted by the corresponding shRNA is GCCCUUAU- CAAGUAUAUAUGGAAA, [SEQ ID NO.: 1] and the shRNA target sequence in CDK19 mRNA is AGGACUGAUAGCUCUUCUUUA [SEQ ID NO.: 2]. Control LKO.1 lentivirus (carrying the puromycin resistance marker) and lentiviruses expressing CDK8 and CDK19 shRNAs, alone or in combination, were generated by transfection with ViraPower lentiviral packaging mix into 293FT cells (Invitrogen), and packaged virus was transduced into the same HT1080-based reporter cell line that was used in the assays shown in FIG. 3. Cell populations, transduced with three different dilutions of the lentivirus-containing supernatant from the transfected packaging cells (1:8, 1:16 and 1:32), were selected with 2 m/ml puromycin and tested for the knockdown of CDK8 and CDK19 mRNA by quantitative reverse transcription-PCR, using the following PCR primers: for CDK8, TGGGATTTCCTGCAGATAAAGATTGGG [SEQ ID NO.: 3] and AGGGGTCCTGCATAGCCTGTT [SEQ ID NO.: 4]; for CDK 19, ACACAAGGTCAAGCCTGACAGCA [SEQ ID NO.: 5] and TGGAATCTGGCAGCCGGCAA [SEQ ID NO.: 6]. As shown in FIG. 9A, CDK8 targeting shRNA decreased CDK8 mRNA level by 65-80% and had no effect on CDK19 mRNA levels, and CDK19 targeting shRNA decreased CDK19 mRNA level by ~75% and had no effect on CDK8 mRNA levels. Co-transduction with CDK8 and CDK19-targeting shRNA had a moderate effect on both mRNAs (35-65% knockdown) (FIG. 9A). We then assayed the untransduced and lentivirus-transduced cell populations for CMV-GFP expression, in the presence and in the absence of IPTG (which induces p21 expression). Two types of assays were used for this analysis. The first assay was the same 96-well plate assay, which measures GFP fluorescence normalized by DNA content; the assays were conducted conducted using either 501.1M IPTG (FIG. 9B) or 41.1M IPTG (FIG. 9C), providing for different levels of p21 induction. The second assay was a flow cytometric assay, where GFP expression was measured by fluorescence using FACS, and dead cells (as defined by propidium iodide uptake) or cells that lost GFP expression were excluded from the analysis. The mean fluorescence intensity of live GFP-positive cells in each population is plotted in FIG. 9D. Both assays produced the same results: the knockdown of CDK8 alone or of both CDK8 and CDK19 decreased IPTG-induced CMV-GFP expression, whereas the knockdown of CDK19 alone not only failed to decrease such expression but in fact moderately increased it in the absence of IPTG. The opposite effects of CDK8 and CDK19 knockdown in our system parallel the findings of Tsutsui et al. (2008) who found through siRNA knockdown assays that CDK8 is a positive regulator but CDK19 is a negative regulator of viral activator VP16-dependent transcription. Hence, CDK8 but not CDK19 is the target of SNX2-class compounds responsible for their activity as CDKI pathway inhibitors.

Example 6

Comparison of Kinase Inhibition and Cell Line Inhibition Profiles of Cortistatin A and SNX2-Class Compounds Table 3 shows the data on the effects of cortistatin A (the only published compound that inhibits CDK8 and CDK19 preferentially to other CDKs) on the activity of 15 kinases that were the most sensitive to this compound. The data from Cee et al. (2009), expressed as POC in the presence of 10 μM cortistatin A, are shown next to our data on the effects of 10 μM compound 1 on the same kinases; both Cee et al. (2009) and we used the same kinome profiling service (KinomeScan). It is apparent from Table 3 that, aside from the inhibition of CDK19 and CDK8, the kinase sensitivity profiles of the two compounds are very different. In particular, cortistatin A decreased ROCK2 binding to 0 POC % and ROCK1 binding to 21 POC, whereas the corresponding values for compound 1 were 89 POC and 79 POC, respectively.

TABLE 3

Kinase inhibition by cortistatin A and SNX2-class compound.

| Kinase | POC Cortistatin A | POC Compound 1 |
| --- | --- | --- |
| ROCK2 | 0 | 89 |
| CDK19 | 0.1 | 0.05 |
| CDK8 | 0.95 | 0.75 |
| LTK | 2.9 | 100 |
| ALK | 4.4 | 78 |
| PIM2 | 4.4 | 52 |
| PKACa | 8.7 | 82 |
| PKACb | 13 | 89 |
| MET | 18 | 86 |
| PRKG2 | 21 | 85 |
| RIOK2 | 21 | 23 |
| ROCK1 | 21 | 79 |
| CLK4 | 26 | 8 |
| ROS1 | 26 | 63 |
| CIT | 28 | 15 |
| JNK1 | 29 | 45 |

If the biological activity of cortistatin A as a highly selective inhibitor of HUVEC proliferation is due to the inhibition of CDK8 and/or CDK19, then a SNX2-class compound would be expected to show the same selective inhibition of HUVECs. If, on the other hand, HUVEC inhibition is mediated by another activity of cortistatin A, such as ROCK inhibition, a SNX2-class compound should not display a similar selectivity for HUVECs. To test the growth inhibitory effects of compound 1 on HUVECs, we have obtained HUVECs from Lifeline Cell Technology (Oceanside, Calif.) and analyzed the effects of different doses of compound 1 on HUVEC proliferation, in a 3-day MTT (3-(4,5-Dimethylthiazol-2-yl)-2,5-diphenyltetrazolium bromide) assay (FIG. 10A). Compound 1 exhibited a moderate growth-inhibitory effect on HUVEC proliferation, with IC50 of 10.4 μM. Notably, compound 1 concentrations that largely inhibited the CKI pathway, such as 0.625 or 1.25 μM, had little or no effect on HUVEC cell number relative to untreated control. Hence, SNX2-class compounds can inhibit the CKI pathway at the concentrations where they do not affect endothelial cell proliferation. We have also determined the effect of compound 1 on the proliferation of KB-3-1 carcinoma cells, which is one of the cell lines tested by Aoki et al. (2007) for growth inhibition by cortistatin A (FIG. 10B). This analysis yielded IC50 of 44.2 μM, which is only 4.3-fold higher than the IC50 for HUVEC cells, as opposed to the 3,900-fold differential for cortistatin A (Aoki et al., 2007). Hence, SNX2-class compounds do not have the selective endothelial cell inhibitory activity of cortistatin A. It seems most likely that inhibition of endothelial cell proliferation by cortistatin A is mediated by the inhibition of ROCK (which is not inhibited by SNX2-class compounds), since ROCK inhibitors fasudil and Y-27632 were shown to inhibit VEGF-stimulated endothelial cell proliferation, migration, and tube formation (references provided in Cee et al., 2009).

Example 7

Inhibition of Colon Carcinoma Cell Growth by SNX2-Class Compounds

Inhibition of β-catenin, which is positively regulated by CDK8, was reported to inhibit proliferation of some colon carcinoma cell lines (Firestein et al., 2008). We have therefore determined the ability of compound 1 to inhibit the proliferation of several colon carcinoma cell lines, including human DLD1, HCT116, SW480 and murine C26. This analysis waqs carried out by incubating cells for 72 hrs in the presence of 0, 2.5, 5 or 10 μM compound 1, followed by FACS measurement of the number of live cells, as defined by the lack of uptake of membrane-impermeable dye propidium iodide. The results shown in FIG. 10C demonstrate that compound 1 inhibited the growth of all four colon carcinoma cell lines, with the strongest growth-inhibitory effect ($IC_{50}$ ~5 μM) found for DLD1 cells, proliferation of which is notably sensitive to β-catenin inhibition (Firestein et al., 2008). This result indicates the utility of CDK8-inhibiting SNX2-class compounds as inhibitors of the growth of tumors expressing β-catenin.

REFERENCES

Reference List

Alarcon, C., Zaromytidou, A. I., Xi, Q., Gao, S., Yu, J., Fujisawa, S., Barlas, A., Miller, A. N., Manova-Todorova, K., Macias, M. J., Sapkota, G., Pan, D., and Massague, J. (2009). Nuclear CDKs drive Smad transcriptional activation and turnover in BMP and TGF-beta pathways. Cell 139, 757-769.

Aoki, S., Watanabe, Y., Tanabe, D., Arai, M., Suna, H., Miyamoto, K., Tsujibo, H., Tsujikawa, K., Yamamoto, H., and Kobayashi, M. (2007). Structure-activity relationship and biological property of cortistatins, anti-angiogenic spongean steroidal alkaloids. Bioorg. Med. Chem. 15, 6758-6762.

Cee, V. J., Chen, D. Y., Lee, M. R., and Nicolaou, K. C. (2009). Cortistatin A is a high-affinity ligand of protein kinases ROCK, CDK8, and CDK11. Angew. Chem. Int. Ed Engl. 48, 8952-8957.

Donner, A. J., Szostek, S., Hoover, J. M., and Espinosa, J. M. (2007). CDK8 is a stimulus-specific positive coregulator of p53 target genes. Mol. Cell. 27, 121-133.

Firestein, R., Bass, A. J., Kim, S. Y., Dunn, I. F., Silver, S. J., Guney, I., Freed, E., Ligon, A. H., Vena, N., Ogino, S., Chheda, M. G., Tamayo, P., Finn, S., Shrestha, Y., Boehm, J. S., Jain, S., Bojarski, E., Mermel, C., Barretina, J., Chan, J. A., Baselga, J., Tabernero, J., Root, D. E., Fuchs, C. S., Loda, M., Shivdasani, R. A., Meyerson, M., and Hahn, W. C. (2008). CDK8 is a colorectal cancer oncogene that regulates beta-catenin activity. Nature 455, 547-551.

Firestein, R. and Hahn, W. C. (2009). Revving the Throttle on an oncogene: CDK8 takes the driver seat. Cancer Res 69, 7899-7901.

Grothey, A. and Galanis, E. (2009). Targeting angiogenesis: progress with anti-VEGF treatment with large molecules. Nat. Rev. Clin. Oncol. 6, 507-518.

Malumbres, M., Harlow, E., Hunt, T., Hunter, T., Lahti, J. M., Manning, G., Morgan, D. O., Tsai, L. H., and Wolgemuth, D. J. (2009). Cyclin-dependent kinases: a family portrait. Nat. Cell Biol. 11, 1275-1276.

Morris, E. J., Ji, J. Y., Yang, F., Di Stefano, L., Herr, A., Moon, N. S., Kwon, E. J., Haigis, K. M., Naar, A. M., and Dyson, N. J. (2008). E2F1 represses beta-catenin transcription and is antagonized by both pRB and CDK8. Nature 455, 552-556.

Sato, S., Tomomori-Sato, C., Parmely, T. J., Florens, L., Zybailov, B., Swanson, S. K., Banks, C. A., Jin, J., Cai, Y., Washburn, M. P., Conaway, J. W., and Conaway, R. C. (2004). A set of consensus mammalian mediator subunits identified by multidimensional protein identification technology. Mol. Cell. 14, 685-691.

Tsutsui, T., Umemura, H., Tanaka, A., Mizuki, F., Hirose, Y., and Ohkuma, Y. (2008). Human mediator kinase subunit CDK11 plays a negative role in viral activator VP16-dependent transcriptional regulation. Genes Cells 13, 817-826.

Westerling, T., Kuuluvainen, E., and Makela, T. P. (2007). Cdk8 is essential for preimplantation mouse development. Mol. Cell. Biol. 27, 6177-6182.

---

What is claimed is:

1. A compound represented by the structural formula:

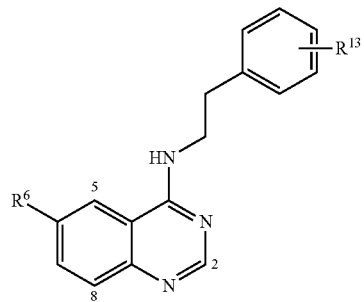

wherein $R^6$ is CN, wherein $R^{13}$ is selected from the group consisting of 2-, 3-, or 4-H, F, Cl, Br, I, OH, $OCH_3$, $CH_3$, $CF_3$, $NR^{11}R^{12}$, $CH_2R^{11}R^{12}$, $CO_2H$ and $CONR^{11}R^{12}$;

and each $R^{11}$ and $R^{12}$ is independently H or C1-C6 alkyl, or $R^{11}$ and $R^{12}$ taken together form a ring.

2. The compound according to claim 1, wherein $R^{13}$ is $CONR^{11}R^{12}$.

3. The compound according to claim 1, wherein $R^{11}$ and $R^{12}$ taken together form a ring.

4. The compound according to claim 1, wherein $R^{13}$ is selected from the group consisting of 2-, 3-, or 4-H and Cl.

5. The compound according to claim 1, wherein $R^{13}$ is Cl.

6. The compound according to claim 1, wherein $R^{13}$ is H.

* * * * *

SEQUENCE LISTING

```
<160> NUMBER OF SEQ ID NOS: 6

<210> SEQ ID NO 1
<211> LENGTH: 24
<212> TYPE: RNA
<213> ORGANISM: Homo sapiens

<400> SEQUENCE: 1
gcccuuauca aguauauaug gaaa                                             24

<210> SEQ ID NO 2
<211> LENGTH: 21
<212> TYPE: RNA
<213> ORGANISM: Homo sapiens

<400> SEQUENCE: 2
aggacugaua gcucuucuuu a                                                21

<210> SEQ ID NO 3
<211> LENGTH: 27
<212> TYPE: DNA
<213> ORGANISM: Homo sapiens
```

```
<400> SEQUENCE: 3
tgggatttcc tgcagataaa gattggg                                    27

<210> SEQ ID NO 4
<211> LENGTH: 21
<212> TYPE: DNA
<213> ORGANISM: Homo sapiens

<400> SEQUENCE: 4
aggggtcctg catagcctgt t                                          21

<210> SEQ ID NO 5
<211> LENGTH: 23
<212> TYPE: DNA
<213> ORGANISM: Homo sapiens

<400> SEQUENCE: 5
acacaaggtc aagcctgaca gca                                        23

<210> SEQ ID NO 6
<211> LENGTH: 20
<212> TYPE: DNA
<213> ORGANISM: Homo sapiens

<400> SEQUENCE: 6
tggaatctgg cagccggcaa                                            20
```